(12) United States Patent  
Roberts et al.

(10) Patent No.: US 9,061,117 B2
(45) Date of Patent: Jun. 23, 2015

(54) CATHETER SYSTEMS AND METHODS OF USE

(75) Inventors: John Robert Roberts, Brentwood, TN (US); Eliot Frank Bloom, Hopkinton, NH (US); Donald Earles, Portsmouth, NH (US)

(73) Assignee: John R. Roberts, Nashville, TN (US)

( * ) Notice: Subject to any disclaimer, the term of this patent is extended or adjusted under 35 U.S.C. 154(b) by 483 days.

(21) Appl. No.: 13/083,464

(22) Filed: Apr. 8, 2011

(65) Prior Publication Data

US 2012/0259206 A1    Oct. 11, 2012

(51) Int. Cl.
*A61B 7/00*    (2006.01)
*A61M 25/01*    (2006.01)
*A61M 16/04*    (2006.01)

(52) U.S. Cl.
CPC ....... *A61M 25/0105* (2013.01); *A61M 16/0488* (2013.01); *A61M 2025/0166* (2013.01); *A61M 2205/3375* (2013.01); *A61M 16/0434* (2013.01); *A61M 16/0463* (2013.01); *A61M 2205/32* (2013.01); *A61M 2205/583* (2013.01); *A61M 2205/6045* (2013.01); *A61M 16/0418* (2014.02); *A61M 16/0484* (2014.02); *A61M 16/0486* (2014.02)

(58) Field of Classification Search
USPC .......................................... 600/514, 528, 586
See application file for complete search history.

(56) References Cited

U.S. PATENT DOCUMENTS

| 2,862,498 | A | | 12/1958 | Weekes | |
|---|---|---|---|---|---|
| 2,949,910 | A | * | 8/1960 | Brown et al. | 600/528 |
| 3,858,575 | A | * | 1/1975 | Rose | 600/528 |
| 4,344,436 | A | | 8/1982 | Kubota | |
| 4,488,548 | A | | 12/1984 | Agdanowski | |
| 4,502,482 | A | | 3/1985 | DeLuccia | |
| 4,512,765 | A | | 4/1985 | Muto | |
| 4,716,896 | A | | 1/1988 | Ackerman | |
| 4,777,961 | A | * | 10/1988 | Saltzman | 600/528 |
| 4,840,172 | A | | 6/1989 | Augustine et al. | |
| 5,135,490 | A | | 8/1992 | Strickland | |
| 5,246,012 | A | | 9/1993 | Strickland | |

(Continued)

FOREIGN PATENT DOCUMENTS

EP    1 767 182 A1    3/2007
GB    2 397 229 A    7/2004

(Continued)

OTHER PUBLICATIONS

"Vibration", NDT Resource Center, Mar. 5, 2008, http://www.ndt-ed.org/EducationResources/HighSchool/Sound/vibration.htm.*

(Continued)

*Primary Examiner* — Sean Dougherty
*Assistant Examiner* — Daniel Cerioni
(74) *Attorney, Agent, or Firm* — Venable LLP; Michele V. Frank, Esq.

(57) ABSTRACT

A catheter system can include a first catheter having an elongated body that defines a lumen, and a second catheter slidably disposed within the lumen of the first catheter. The second catheter can include an acoustic device. The acoustic device can create a sound for verifying the location of the second catheter within a body lumen. The distal end portion of the second catheter can include a pre-formed bend that extends at a non-zero angle relative to a longitudinal axis of the first catheter. In some embodiments, the second catheter can be used to aspirate a substance from a body lumen.

7 Claims, 13 Drawing Sheets

(56) References Cited

U.S. PATENT DOCUMENTS

| | | | |
|---|---|---|---|
| 5,606,968 A | | 3/1997 | Mang |
| 5,660,175 A | | 8/1997 | Dayal |
| 5,775,322 A | * | 7/1998 | Silverstein et al. ...... 128/207.14 |
| 5,844,997 A | * | 12/1998 | Murphy, Jr. ..................... 381/92 |
| 6,053,166 A | | 4/2000 | Gomez |
| 6,064,902 A | | 5/2000 | Haissaguerre et al. |
| 6,306,097 B1 | | 10/2001 | Park et al. |
| 6,349,720 B1 | * | 2/2002 | Clark ....................... 128/200.26 |
| 6,443,156 B1 | | 9/2002 | Niklason et al. |
| 6,513,527 B1 | | 2/2003 | Abdel-Aziz |
| 6,568,393 B2 | | 5/2003 | Christopher |
| 7,097,643 B2 | | 8/2006 | Cornelius et al. |
| 2003/0018276 A1 | * | 1/2003 | Mansy et al. ................. 600/529 |
| 2005/0103332 A1 | | 5/2005 | Gingles et al. |
| 2005/0197623 A1 | | 9/2005 | Leeflang et al. |
| 2006/0241564 A1 | | 10/2006 | Corcoran et al. |
| 2007/0010762 A1 | | 1/2007 | Ressemann et al. |
| 2007/0078463 A1 | * | 4/2007 | Malandain ...................... 606/80 |
| 2009/0118612 A1 | * | 5/2009 | Grunwald et al. ............ 600/424 |
| 2009/0187164 A1 | | 7/2009 | Rowe |
| 2009/0248045 A1 | | 10/2009 | Trovato |
| 2009/0292209 A1 | | 11/2009 | Hadjicostis |
| 2010/0198141 A1 | * | 8/2010 | Laitenberger et al. .......... 604/65 |
| 2010/0300449 A1 | | 12/2010 | Chan et al. |
| 2011/0201887 A1 | | 8/2011 | Greenblatt et al. |
| 2011/0245665 A1 | | 10/2011 | Nentwick |
| 2012/0259208 A1 | | 10/2012 | Bloom et al. |

FOREIGN PATENT DOCUMENTS

| | | |
|---|---|---|
| WO | WO 97/49445 A1 | 12/1997 |
| WO | 2007/008332 A2 | 1/2007 |
| WO | 2008/032230 A1 | 3/2008 |
| WO | 2010/044051 A1 | 4/2010 |

OTHER PUBLICATIONS

Airwaycam.com, Tracheal Tube Design and Delivery, http://www.airwaycam.com/intubation-Endotracheal-Tube-design.html, Copyright 2011, last accessed Jun. 24, 2011, 2 pages.

M. K. Sykes, Improved Plastic Endotracheal Tubes, British Medical Journal, Apr. 20, 1968, 1 page.

Co-pending U.S. Appl. No. 13/083,462, to Roberts et al., filed Apr. 8, 2011.

International Search Report and Written Opinion for International Appl. No. PCT/US2011/062438, European Patent Office, The Netherlands, mailed on Jun. 11, 2012, 24 pages.

PCT/US2011/062440: International Search Report and Written Opinion dated Jun. 11, 2012.

PCT/US2012/032547: International Search Report and Written Opinion dated Jan. 28, 2013.

PCT/US2014/029265: International Search Report and Written Opinion mailed Oct. 24, 2014.

* cited by examiner

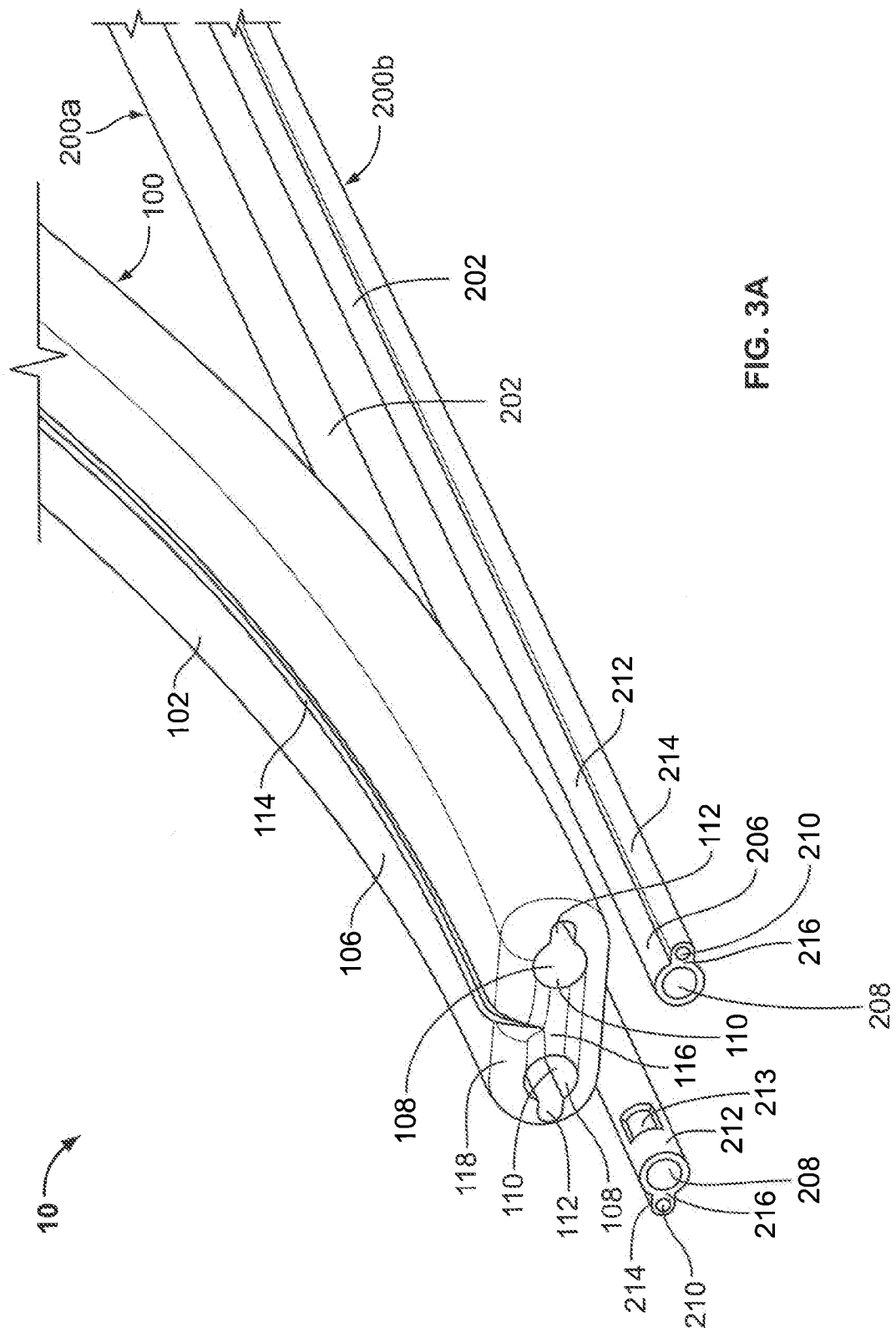

CATHETER SYSTEMS AND METHODS OF USE

CROSS-REFERENCE TO RELATED APPLICATION

This application shares a common disclosure with commonly-owned, co-pending U.S. patent application Ser. No. 13/083,462 filed Apr. 8, 2011, which is incorporated herein by reference in its entirety.

BACKGROUND

1. Field

The present invention relates to medical devices and, in particular, to catheters that can easily be advanced into tortuous body lumens and for which the location of the catheters within body lumens can easily be verified.

2. Background Art

Medicine is providing ever-increasing demands for devices that can navigate narrow passageways to a desired location within a body so that diagnostic and therapeutic procedures can be performed at that location. Currently, elongated medical devices such as catheters can extend into a body from outside via an access point through various connected passageways to a target location.

One example of a tortuous pathway is the respiratory tract. The respiratory tract begins at the nose and mouth, which open to the trachea. The trachea travels downward into the chest at which it splits into the left and right main bronchi. The left and right main bronchi split at an angle from the trachea. The left main bronchus can be smaller in diameter than the right main bronchus and branches at a greater angle from the trachea than the angle at which the right main bronchus branches from the trachea. The main bronchi then split into lobar bronchi, which split into segmental bronchi. The segmental bronchi split into subsegmental bronchi.

Numerous procedures require intubation of the respiratory tract, including the left and right main bronchi, to aspirate mucus in the lungs or to delivery localized medicine, for example. Intubation of the left main bronchus from the trachea can be difficult because it can have a smaller diameter and greater angle relative to the trachea. For example, a typical procedure for aspirating fluid from the lungs can include introducing an endotracheal tube to the trachea of a patient, followed by extending a working catheter (e.g., an aspiration catheter) through a lumen of the endotracheal tube and into either the right or left main bronchus. Respiratory therapists seeking to intubate the left main bronchus with the aspiration catheter may mistakenly believe the left main bronchus has been intubated, when the catheter has actually entered the right main bronchus instead. In some instances, the endotracheal tube can be mistakenly inserted too deep so that its distal end extends into the right main bronchus, whereby the aspiration catheter can only access the right main bronchus. Often times, a specialist, such as a pulmonologist, is needed to insert a bronchoscope into the left main bronchus and aspirate the left main bronchus using the working channel of the bronchoscope. The bronchoscope is equipped with a vision system (including, for example, a fiberoptic system) and/or a fluoroscopic imaging system, to guide the bronchoscope into the left main bronchus. However, visualization equipment and the endoscopic procedure can be expensive, and specialists may not be readily available to conduct the procedure when desired.

BRIEF SUMMARY

What is needed is a catheter system having an outer delivery catheter and an inner working catheter (e.g., an aspiration catheter) that can easily intubate a chosen body lumen (e.g., the left main bronchus), without requiring an endoscopic procedure to ensure that the working catheter has actually entered the chosen body lumen (e.g., the left main bronchus), and not another lumen (e.g., the right main bronchus). Also what is needed is a catheter system in which the desired placement of a working catheter within a chosen body lumen can be easily verified without using endoscopy to assure placement.

In some embodiments a catheter can include an elongated body having a proximal end portion and a distal end portion. The elongated body can define a lumen extending from the proximal end portion to the distal end portion. The catheter can also include an acoustic device that creates a sound at the distal end portion of the elongated body for verifying the location of the distal end portion within a body lumen.

In some embodiments, a catheter system can include a first catheter. The first catheter can include a first elongated body having a first proximal end portion, a first distal end portion, and a lumen extending from the first proximal end portion to the first distal end portion. The catheter system can also include a second catheter slidably disposed within the first lumen of the first catheter. The second catheter can include a second elongated body having a second proximal end portion, a second distal end portion, and a lumen extending from the second proximal end portion to the second distal end portion. The second catheter can also include an acoustic device that creates a sound at the second distal end portion of the second catheter for verifying the location of the second distal end portion of the second catheter within a body lumen.

In some embodiments, a catheter can include an elongated body having a proximal end portion and a distal end portion. The elongated body can define a lumen extending from the proximal end portion to the distal end portion. The distal end portion of the elongated body includes a pre-formed bend that is configured to extend at a non-zero angle relative to a longitudinal axis of a body lumen when the catheter is disposed in the body lumen. The catheter can also include a directional indicator on the proximal end portion that indicates a radial direction at which the distal end portion extends from the longitudinal axis.

Methods for using catheters catheter systems according to embodiments described herein are also provided.

BRIEF DESCRIPTION OF THE DRAWINGS/FIGURES

Embodiments of the present invention are described with reference to the accompanying drawings. In the drawings, like reference numbers indicate identical or functionally similar elements.

Figure 1:
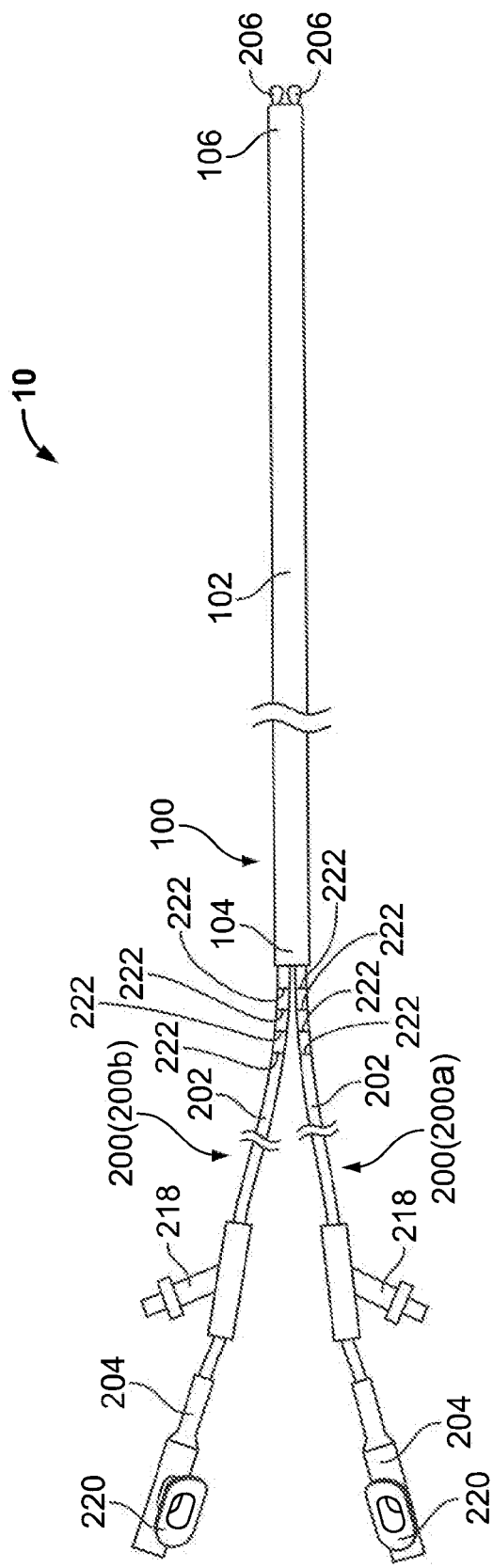
FIG. 1 illustrates a plan view of a catheter system including an outer catheter and two inner catheters according to an embodiment presented herein.

FIG. 3A schematically illustrates an exploded, distal perspective view of the catheter system of FIG. 1 showing key joint components of the outer catheter and inner catheters according to an embodiment presented herein.

Figure 3B:
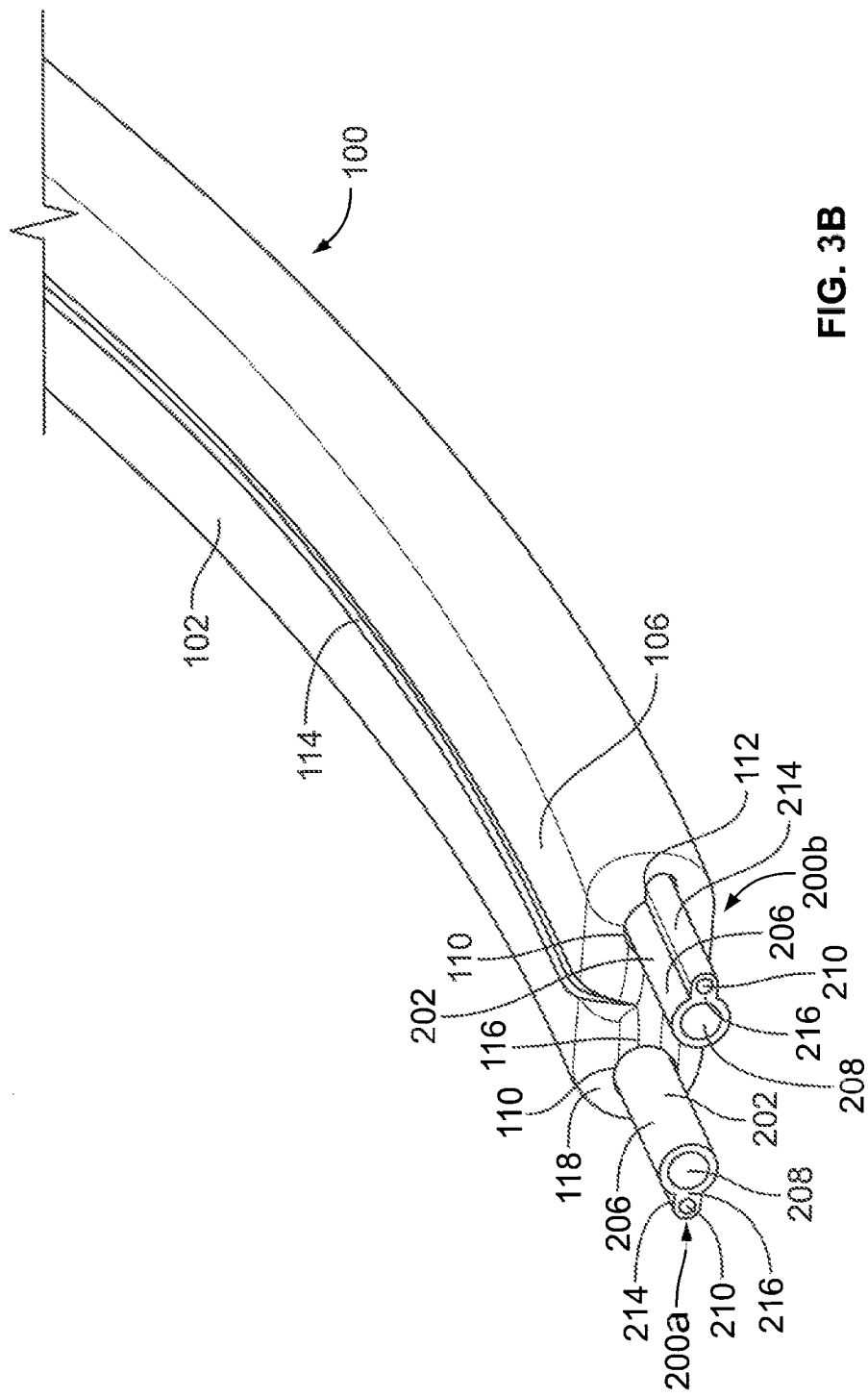

FIG. 3B schematically illustrates the catheter system of FIG. 3A showing the inner catheters disposed in the outer catheter according to an embodiment presented herein.

FIGS. 4A-4D illustrate cross-sectional views of exemplary catheter and lumen configurations for an outer catheter and inner catheter(s) according to embodiments presented herein.

Figure 5:
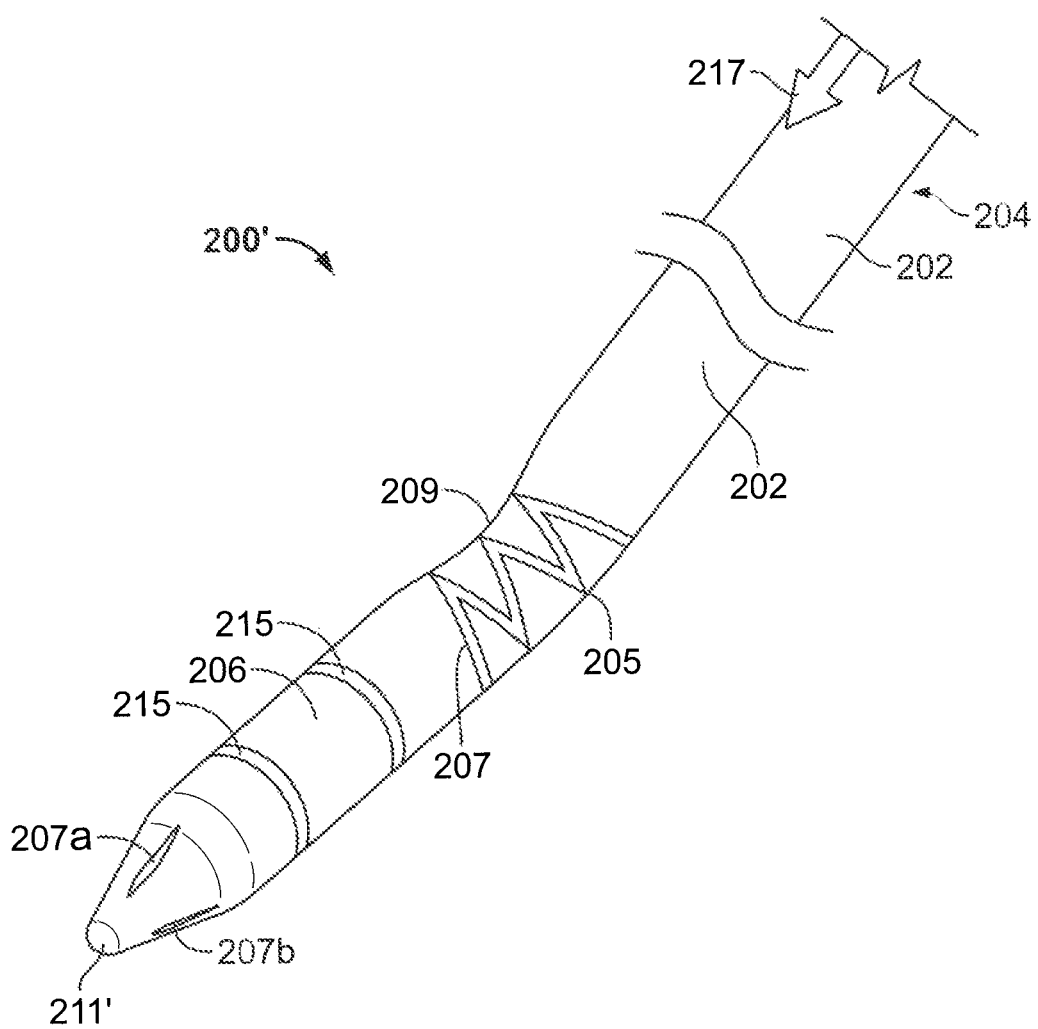

FIG. 5 illustrates a perspective view of an inner catheter having a conical shaped distal end according to an embodiment presented herein.

Figure 6A:
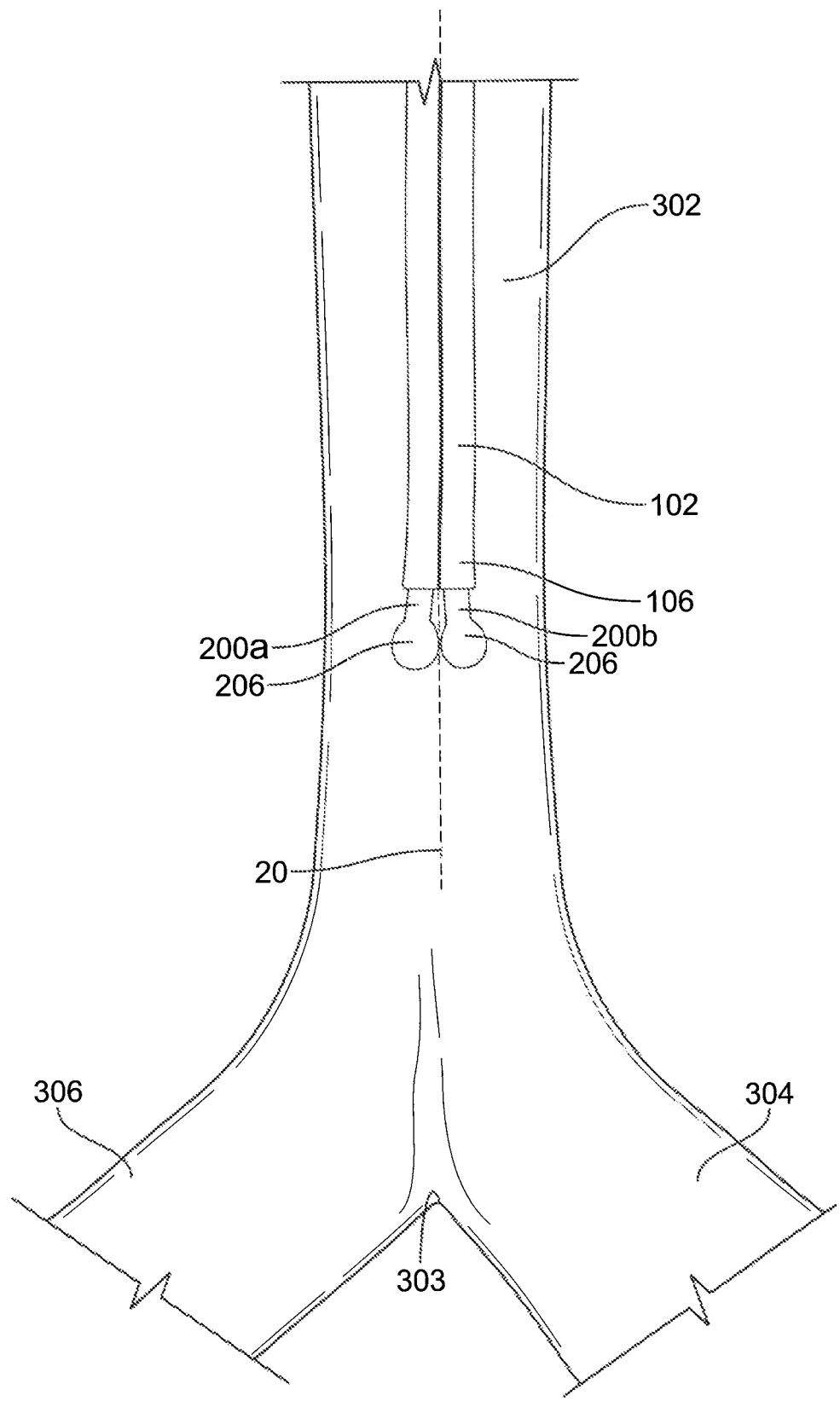

FIG. 6A illustrates the catheter system of FIG. 1 positioned within a trachea according to an embodiment presented herein.

Figure 6B:
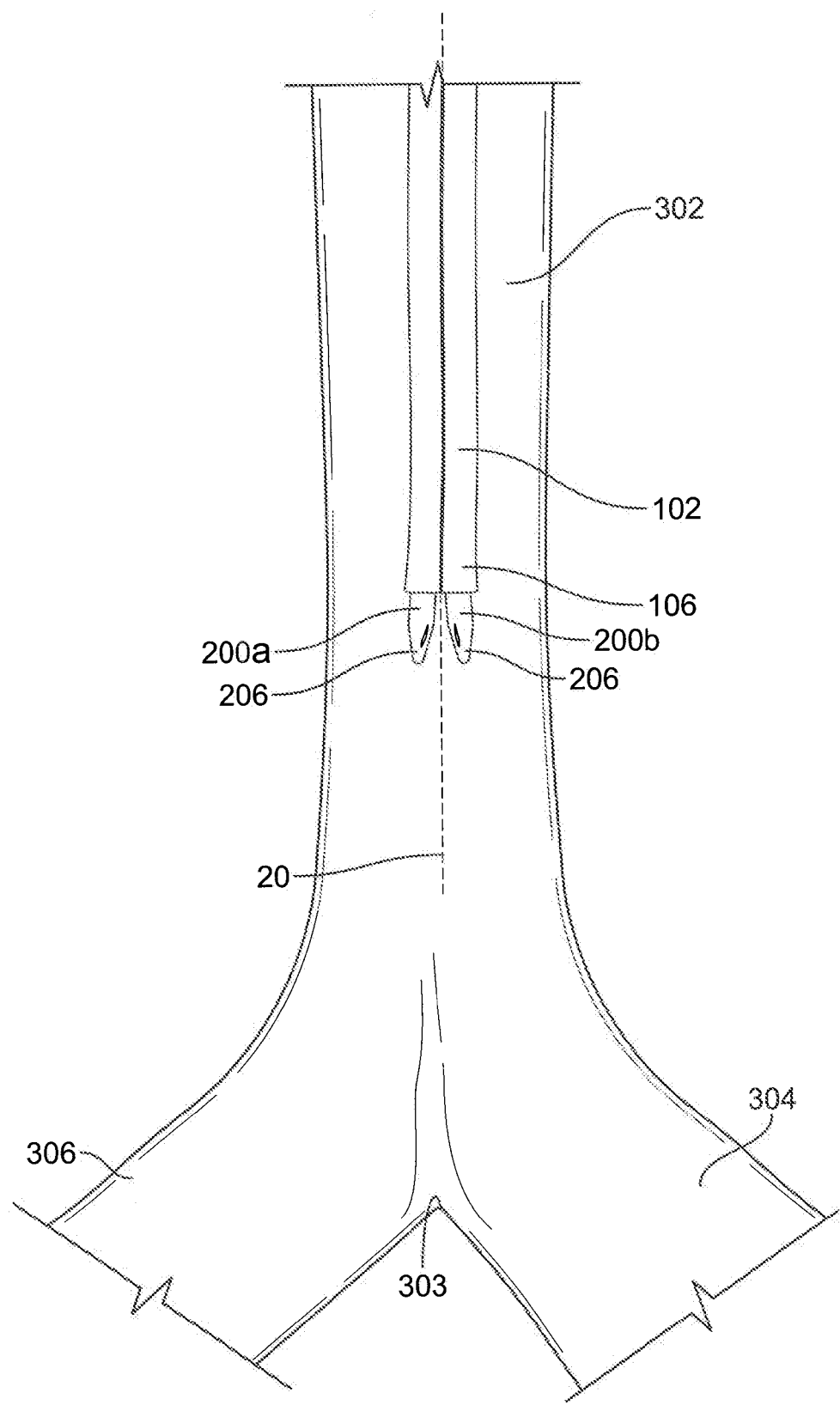

FIG. 6B illustrates the catheter system of FIG. 1 with inner catheters of FIG. 5 within a trachea according to an embodiment presented herein.

Figure 7:
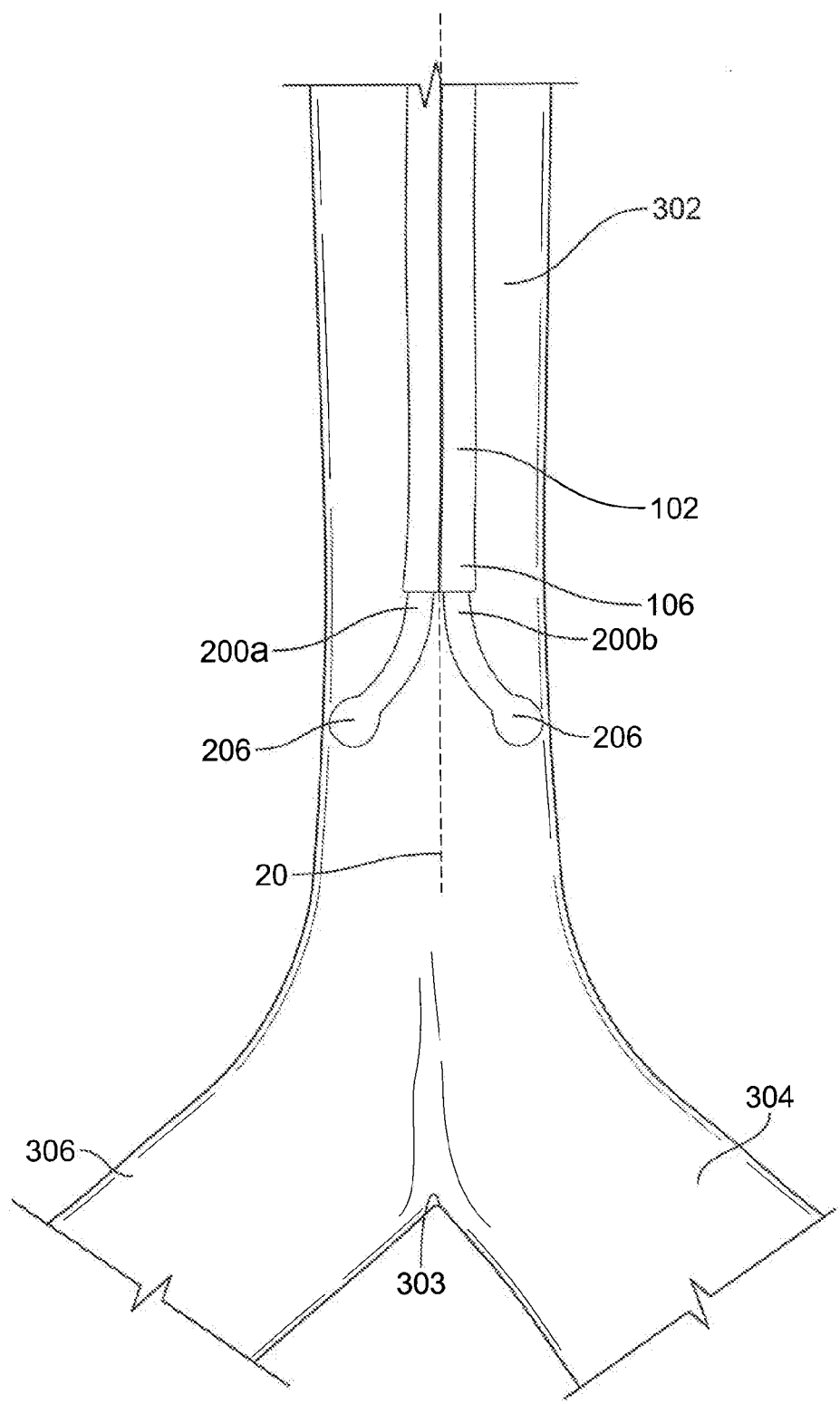

FIG. 7 illustrates the catheter system of FIG. 1 in which the distal end portions of the two inner catheters are extended from the distal end of the outer catheter according to an embodiment presented herein.

Figure 8:
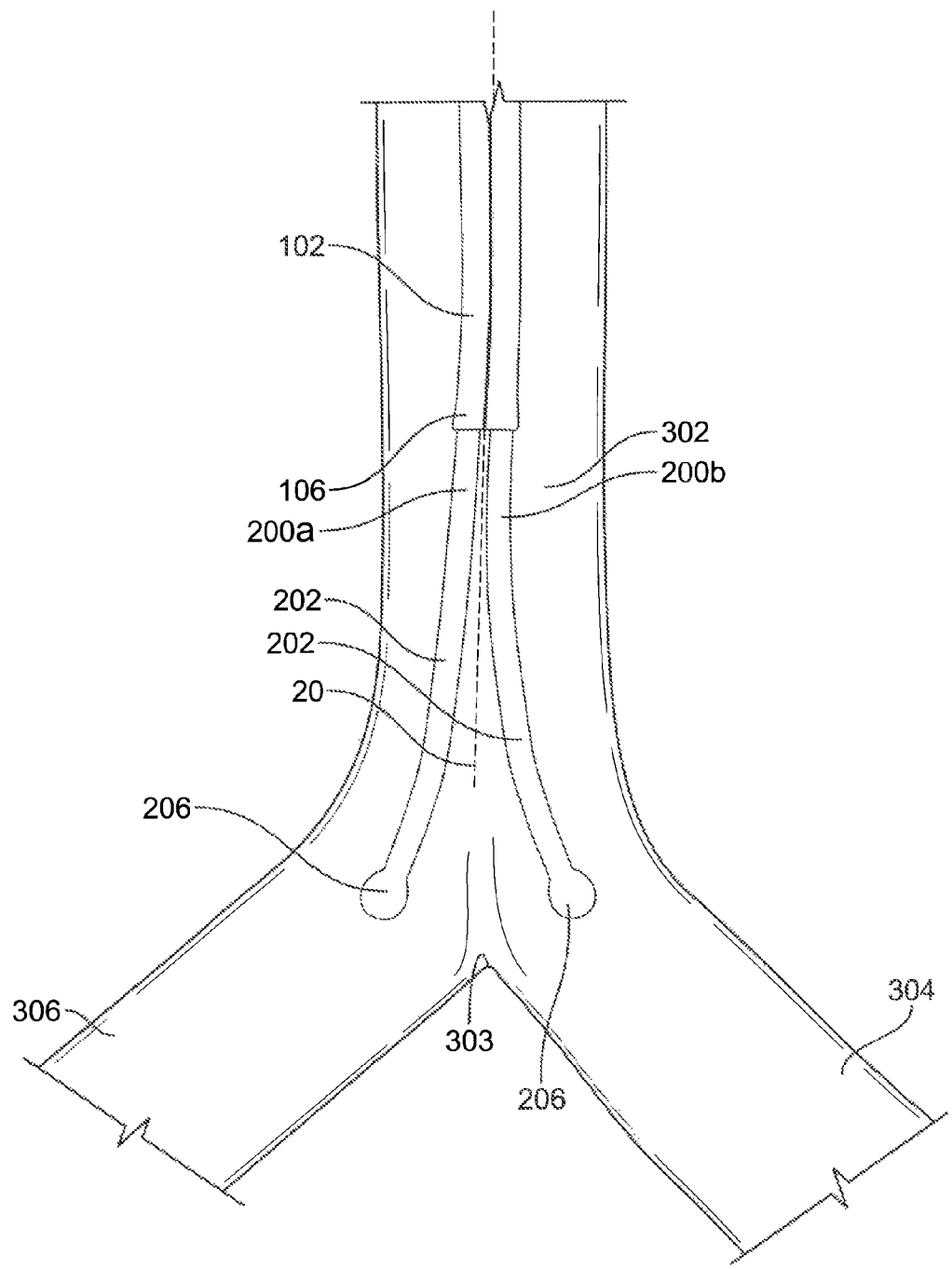

FIG. 8 illustrates the catheter system of FIG. 1 in which the distal end portions of the two inner catheters are extended from the distal end of the outer catheter according to an embodiment presented herein.

Figure 9:
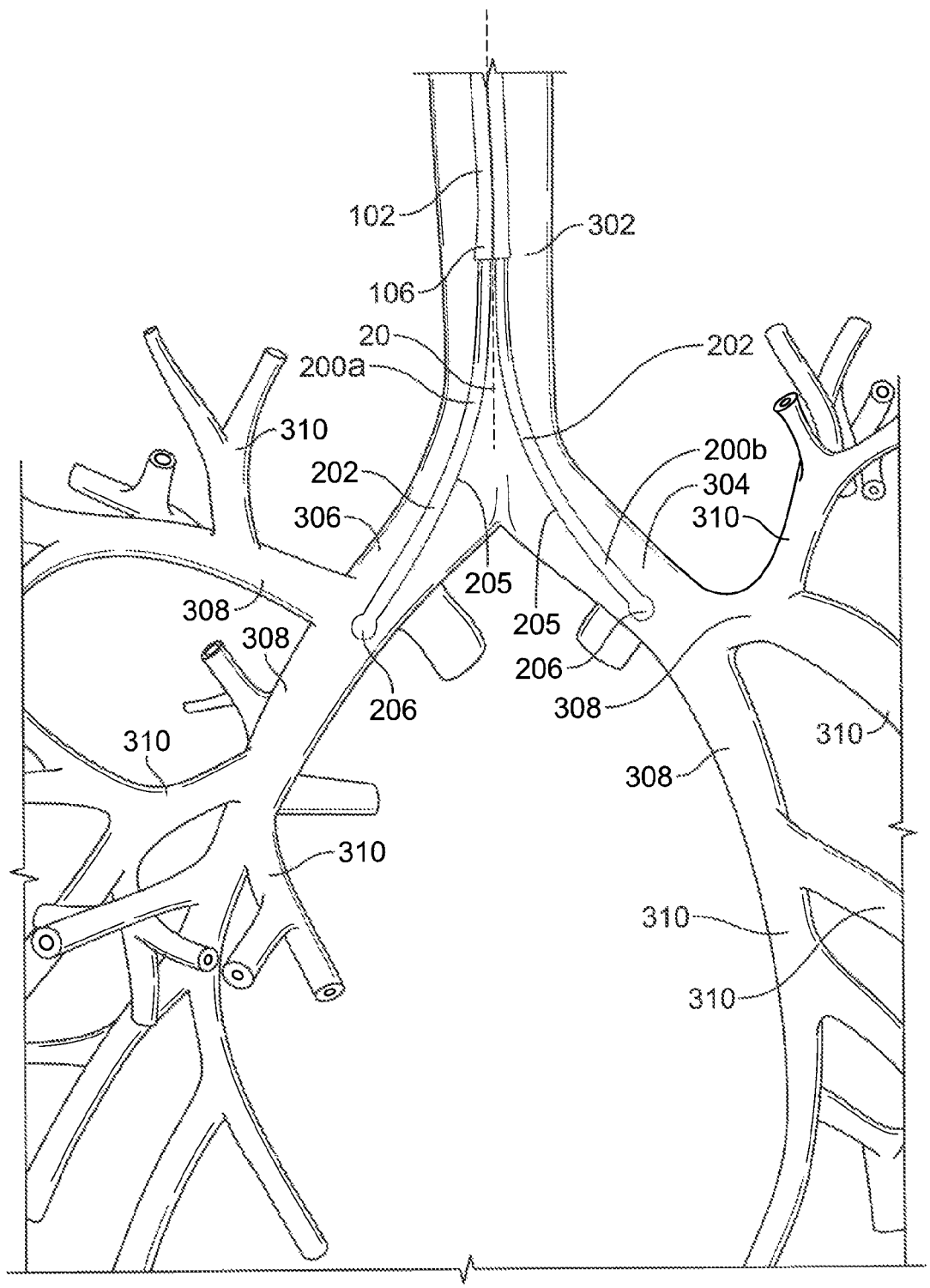

FIG. 9 illustrates the catheter system of FIG. 1 in which the distal end portions of the two inner catheters extend into left and right main bronchi according to an embodiment presented herein.

Figure 10:
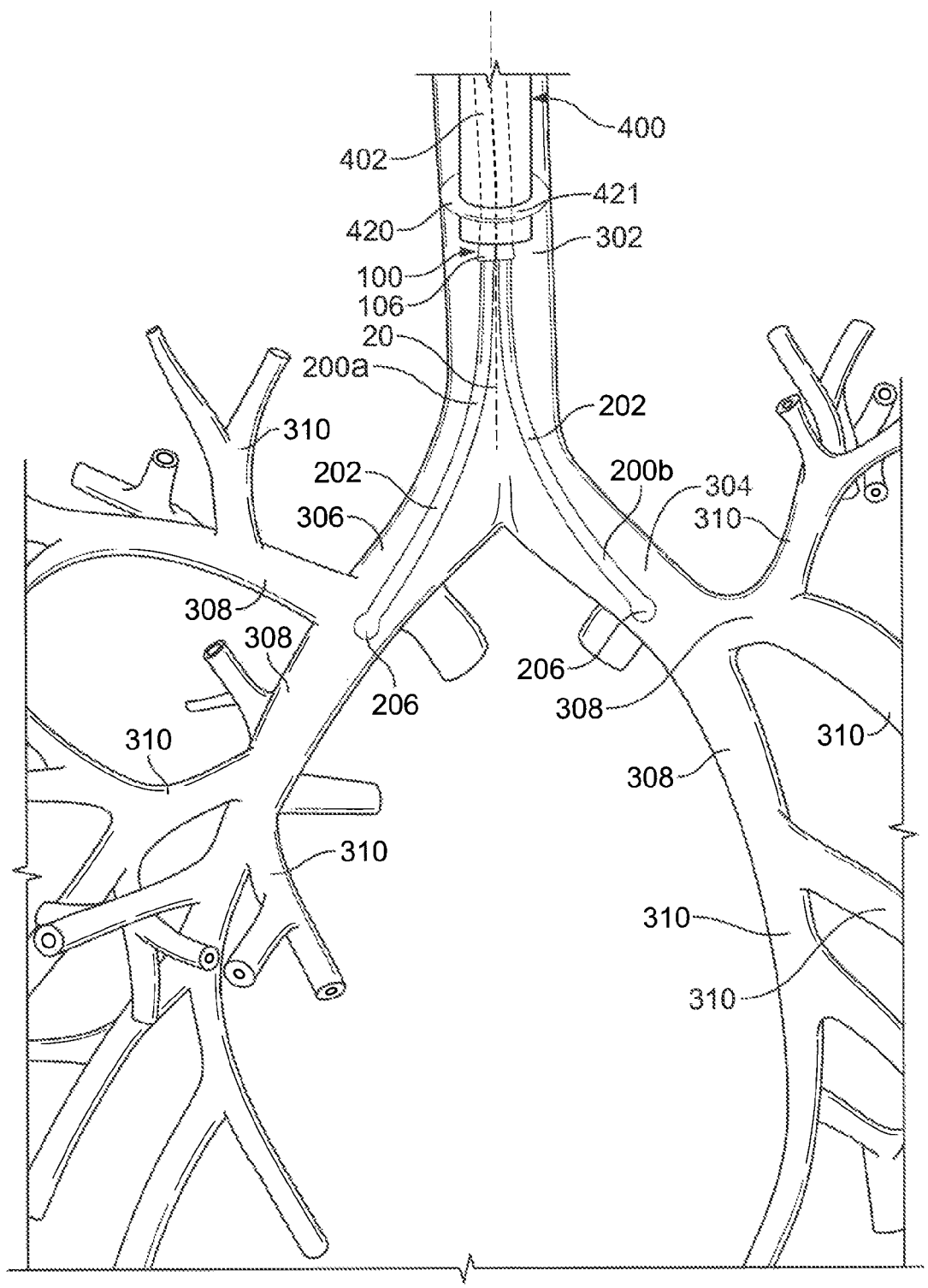

FIG. 10 illustrates the catheter system of FIG. 1 inserted through a third catheter having an expandable support member securing the third catheter in position in the trachea according to an embodiment presented herein.

Figure 11:
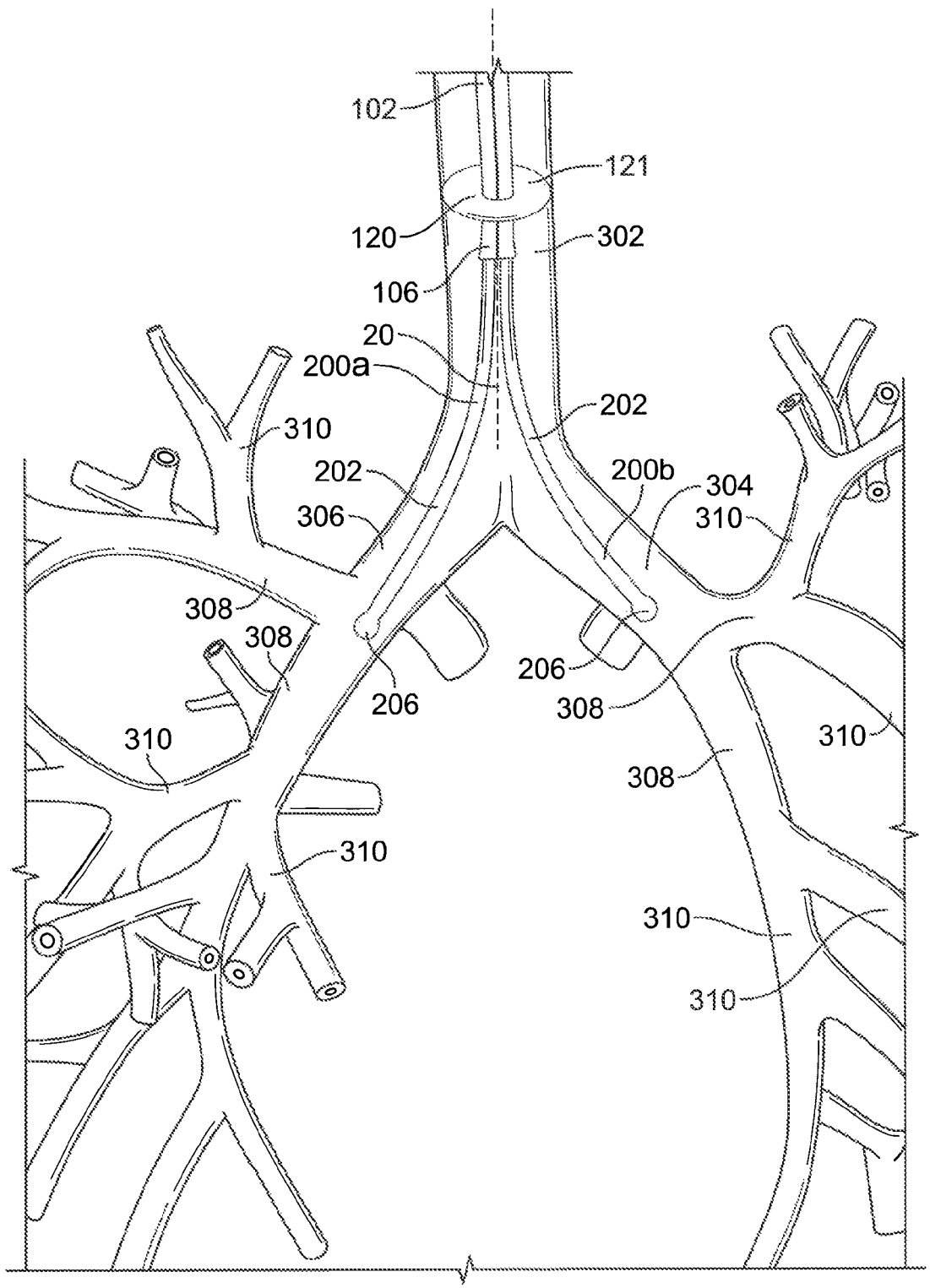

FIG. 11 illustrates the catheter system of FIG. 1 having an expandable support member securing the outer catheter in position in the trachea according to an embodiment presented herein.

Figure 12:
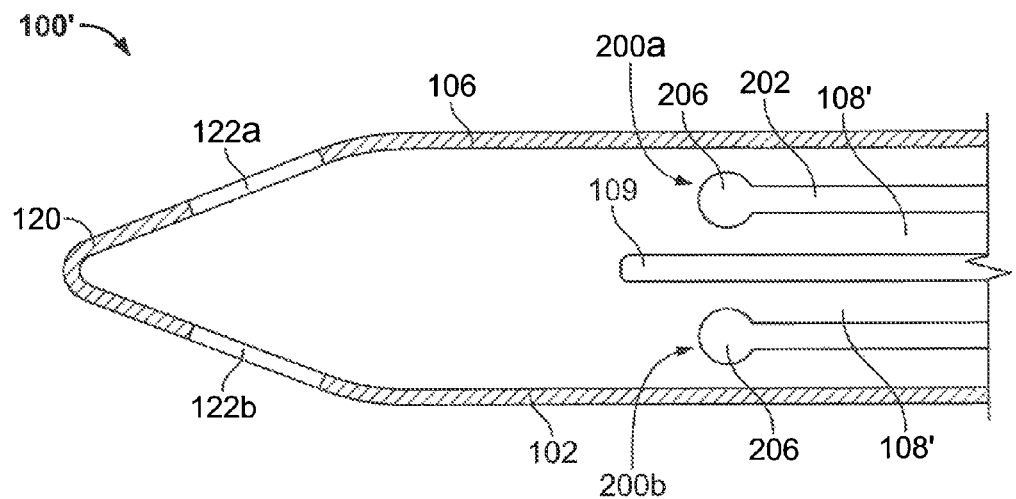

FIG. 12 illustrates a cross-sectional view of a catheter system according to an embodiment presented herein.

Figure 13:
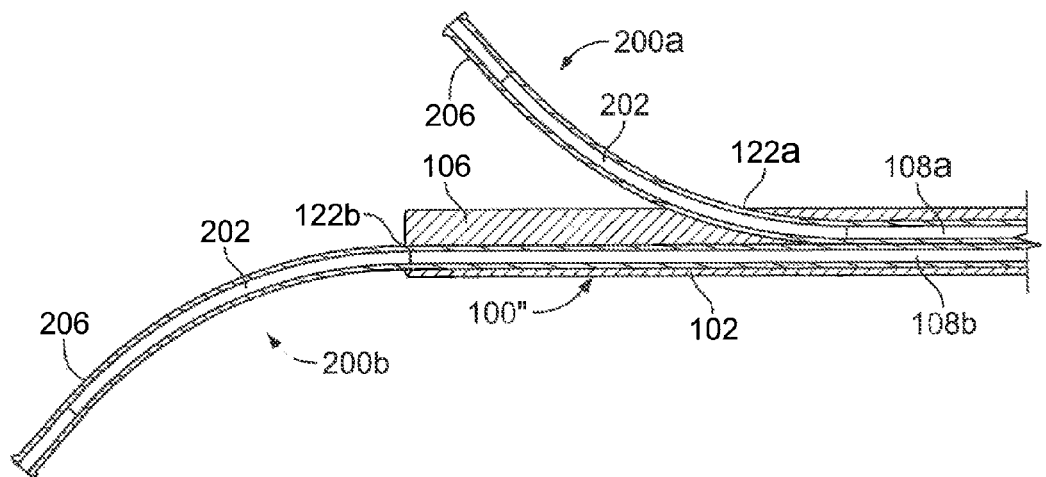

FIG. 13 illustrates a cross-sectional view of a catheter system according to an embodiment presented herein.

The features and advantages of the present invention will become more apparent from the detailed description set forth below when taken in conjunction with the drawings, in which like reference characters identify corresponding elements throughout.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such a feature, structure, or characteristic in connection with other embodiments whether or not explicitly described.

FIGS. 1, 2, 3A, and 3B illustrate a catheter system 10 according to some embodiments. Catheter system 10 can include an outer catheter 100 which slidably receives therein one or more inner catheter(s) 200. In the embodiments shown in the Figures, catheter system 10 includes two inner catheters 200a and 200b. However, it should be understood that the embodiments of catheter system 10 illustrated in the Figures are shown as non-limiting examples only. Thus, in some embodiments, catheter system 10 can be configured to have only one inner catheter 200, or in some embodiments can be configured to have more than two inner catheters without departing from the general concept of the present invention.

Figure 2:
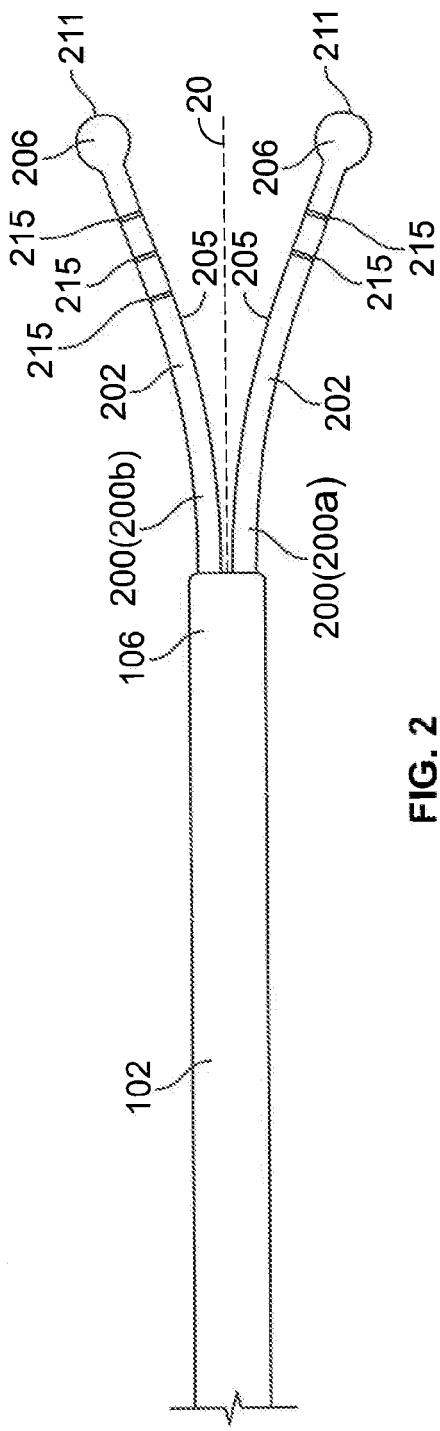
FIG. 2 illustrates a plan view of the catheter system of FIG. 1 according to an embodiment presented herein.

Outer catheter 100 can include an elongated body 102 having a proximal end portion 104 and a distal end portion 106. Elongated body 102 can have a longitudinal axis 20 as illustrated in FIG. 2. Outer catheter 100 can be configured to be inserted in to a body lumen. Elongated body 102 can have a length such that when distal end portion 106 is at a desired target location within a body lumen, proximal end portion 104 is outside the body. For example, outer catheter 100 can be an endotracheal tube having a distal end portion 106 inserted into a trachea through an incision in the throat or through the mouth or nose, and a proximal end portion 104 outside the body.

Elongated body 102 can define one or more lumen(s) 108 extending from proximal end portion 104 to distal end portion 106. Lumen(s) 108 can have openings at proximal end portion 104 and at distal end portion 106. Lumen(s) 108 can slidably receive one or more catheters 200 through the opening at proximal end portion 104. In some embodiments, elongated body 102 can define one lumen 108 configured to slidably receive one or more inner catheters 200. For example, in some embodiments, the one lumen can receive one inner catheter 200, and in some embodiments, the one lumen can receive two inner catheters 200 (such as inner catheters 200a and 200b, as shown in FIGS. 1 and 2). In some embodiments, as shown in FIGS. 3A and 3B, elongated body 102 can define two lumens 108 separated from each other by an intermediate wall portion 116 that can extend the length of elongated body 102. The two lumens 108 are configured to receive one of respective catheters 200a and 200b. Lumen(s) 108 can also include a key joint component that corresponds to a key joint component on inner catheter 200 to fix the rotational orientation of inner catheter relative to outer catheter 100 as later described with reference to FIGS. 3A and 3B. In some embodiments, the outer contour of elongated body 102 can be circular, oval, or any other suitable shape. In some embodiments, the outer contour of elongated body 102 corresponds to the shape of the body lumen in which elongated body 102 passes.

Inner catheter 200 can include an elongated body 202 having a proximal end portion 204 and a distal end portion 206. Elongated body 202 can define one or more lumens having an opening at proximal end portion 204 and an opening at distal end portion 206. For example, elongated body 202 can define a first lumen 208 and a second lumen 210 that extend from proximal end portion 204 to distal end portion 206. At proximal end 204, first lumen 208 can have a port 220, and second lumen 210 can have a port 218. FIG. 1 illustrates port 220 and port 218 of inner catheter 200 according to an embodiment. Port 220 can be configured to couple to a device that creates a suction for removing substances through first lumen 208. Port 218 can be configured to couple to a pump and/or a fluid supply for delivering fluid through second lumen 210. Ports 218 and 220 can be positioned on elongated body 202 such that they remain outside the body when distal end portion 206 is within a body lumen.

First lumen 208 can remove substances from a body lumen, such as blood, mucus, and bodily fluids that reside in the body lumen. For example, in a pulmonary procedure, catheter 200 can be extended into a main bronchus, and first lumen 208 can be used to aspirate mucus from the main bronchus. In some embodiments, second lumen 210 can deliver substances to the body lumen in which distal end portion 206 resides. For example, in some embodiments, second lumen 210 can deliver medicinal fluids in the form of liquids or aerosolized powders and/or aerosolized liquids. Such drug delivery to the lungs can be achieved by inserting distal end portion 206 of second lumen 210 into the trachea, main bronchi, lobar bronchi, segmental bronchi, and the subsegmental bronchi of the respiratory tract, and dispensing a drug into lumen 210 via port 218 at proximal end portion 204, which exits into the lung via the opening of lumen 210 at distal end portion 206. In some embodiments, first lumen 208 can deliver a fluid to flush any substances that may be clogged on first lumen 208 from aspiration. For example, a luer can be coupled to port 220, and flushing fluid can be delivered to lumen 208 via a syringe attached to the luer.

Elongated body 202 can have one or more depth indicators 222 located at proximal end 204. For example, depth indicators 222 can be equally spaced lines that circumscribe elongated body 202, with each indicator 222 providing a measurement of its distance to the distal end portion 206. When distal end portion 206 is inserted into a body lumen, a medical practitioner can read depth indictors 222 at proximal end 204 to determine the depth that distal end portion 206 has been inserted. As such, depth indicators 222 provide the medical practitioner a quick visual verification of the depth distal end portion 206 has been advanced into a body lumen.

In some embodiments, inner catheter 200 can include an acoustic device that creates a sound at distal end portion 206 of elongated body 202 for verifying the location of distal end portion 206 within a body lumen. FIGS. 3A and 3B depict a catheter 200 having an acoustic device that creates a sound at distal end portion 206 of elongated body 202 according to an embodiment. First lumen 208 can remove (e.g., aspirate) fluid in an area within a body lumen that surrounds distal end portion 206. Second lumen 210 of catheter 200 can deliver fluid, for example, a saline solution, to the area surrounding distal end portion 206. First lumen 208 can then be used to remove the fluid delivered from lumen 210 to the area surrounding distal end portion 206. This removal of the fluid can create a sound, for example, a gurgling sound, which serves as the acoustic device. Because the sound is created at distal end portion 206, identifying the location of the sound can verify the location of distal end portion 206 within a body lumen.

In some embodiments, the acoustic device can be an aerophone device, for example, a whistle, or any other device or feature of inner catheter 200 that creates a sound. As shown in FIG. 3A, a slit or edge 213 can be disposed in first lumen 208 which serves as a whistle. Slit or edge 213 is disposed at distal end portion 206 in FIG. 3A. In some embodiments, the slit or edge 213 can be disposed at proximal end portion 204. Thus, the acoustic device that creates the sound can be disposed at proximal end portion 204 or distal end portion 206. In either case, the sound is created at the opening of first lumen 208 at distal end portion 206. In particular, gas or fluid can be passed through first lumen 208, and the passing fluid or gas can go through or by slit or edge 213 causing a vibration in the fluid or gas. This vibration can create a sound at distal end portion 206. In some embodiments, the acoustic device can be a clicker or any other suitable device that can create a sound while within a body lumen.

The sound created by the acoustic device at the distal end portion of the elongated body can be detected with or without a sensing device. For example, in some embodiments, the location of the sound can be detected by using a stethoscope on an outside surface of the body in which catheter 200 is inserted. In some embodiments, the sound can be detected without using the stethoscope.

In some embodiments, instead of or in addition to an acoustic device, a light source can be disposed at distal end portion 206 of elongated body 202 for verifying the location of distal end portion 206 within a body lumen. By detecting the location of the light created by the light source, the location of the distal end portion 206 can be verified.

As shown in FIGS. 3A and 3B, distal end portion 106 of elongated body 102 can have a pre-formed bend that extends away from a longitudinal axis of a body lumen (see, e.g., longitudinal axis 20 shown in FIG. 7, which corresponds with longitudinal axis 20 of elongated body 102 shown in FIG. 2). In some embodiments, the pre-formed bend at distal end portion 106 of outer catheter 100 can correspond to the curvature of the body lumen(s) in which inner catheter 100 is inserted, for example, the curvature of the wind pipe (trachea 302) from the mouth or nose. As such, the pre-formed bend at distal end portion 106 of outer catheter 100 can assist in the insertion of catheter 100 through the nose or mouth to the patient's respiratory tract. Further, when catheter system 10 is configured for insertion into the trachea, the pre-formed bend at distal end portion 106 can help direct the extension of inner catheters 200a and 200b toward main bronchi 304 and 306, by helping to point extended portion of inner catheters 200a and 200b away from longitudinal axis 20 and away from carina 303 (see FIG. 8). As shown in FIGS. 3A and 3B, elongated body 102 can have a visual marker 114 that indicates a direction at which elongated body 102 curves. For example, as shown in FIGS. 3A and 3B, visual marker 114 can be a line 114 or an outer surface of elongated body 102 that is aligned with the curvature of elongated body 102. Visual marker 114 can assist the medical practitioner to adjust the rotational orientation of catheter 100 relative to the body lumen so that bent distal end portion 106 is oriented to face a desired radial direction.

Figure 4A:
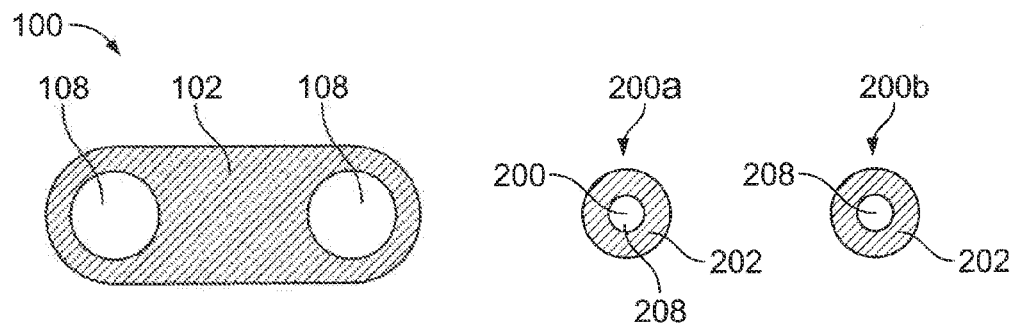
Figure 4B:
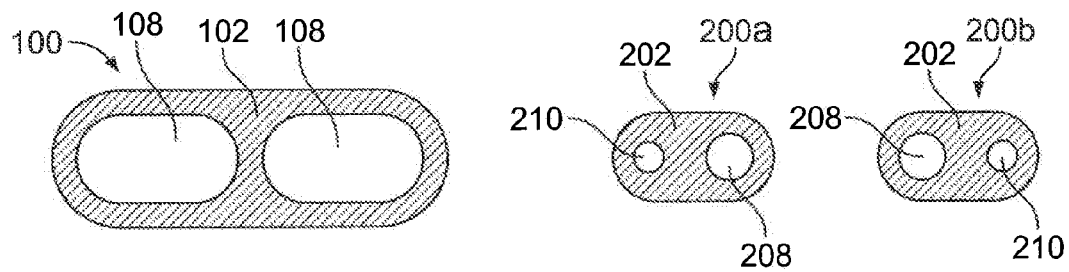

In some embodiments, elongated body 202 of catheter 200 can include a pre-formed bend 205 at distal end portion 206 (see FIG. 2) that causes distal end portion 206 to extend away from a longitudinal axis 20 of a body lumen in which catheter 200 is inserted (see FIG. 9). FIGS. 1, 2, 6, and 7 illustrate catheter 200 having an angled distal end portion 206 according an embodiment in a relaxed or confined position. (FIG. 4A is a schematic illustration that does not show pre-formed bend 205.) Angled distal end portion 206 can be flexible such that it can conform to a straight outer catheter 100 when inserted therein as illustrated in FIGS. 1, 4B, and 5, but bend at a non-zero angle relative to longitudinal axis 20 of the body lumen when distal end portion 206 is positioned outside of distal end portion 106 of outer catheter 100. The pre-formed bend 205 can be formed by two segments of body 202 that intersect at an angle other than zero or non-180 degree angle, or any other suitable non-linear shape. In some embodiments, pre-formed bend 205 can be a curve, such that that the two segments gradually angle toward each other to meet at bend 205 so as to form a curve. In some alternative embodiments, pre-formed bend 205 can be a sharp angle.

Elongated body 202 of inner catheter 200 and elongated body 102 of outer catheter 100 can each be made of any suitable material that provides the appropriate compromise between strength, flexibility, and other requirements. For example, suitable materials that can provide the appropriate compromise between these two extremes include silicones, polyvinylchloride (PVC), polyurethane, elastomeric polyamides, block polyamide (such as Pebax®, a polyether block amide, available from Arkema, Colombes, France), Tecoflex® and various co-polymers. In some embodiments, for each of inner and outer catheters, the desired degree of flexibility can be achieved by material selection (for example, polymers) and thickness selection. Flexibility can also be enhanced by using flexibility mechanisms such as a coiled wire 207 at bend 205 or a living hinge 209 at points were flexibility is required, or a combination thereof, for example (see later described inner catheter 200' shown in FIG. 5).

Pre-formed bend 205 of inner catheter 200 can be formed by inserting a shaped (or curved) mandrel into a lumen defined by elongated body 202 and then heating elongated body 202 with the mandrel in the lumen. After removing the mandrel, elongated body 202 can have a pre-formed bend that corresponds to the shape of the mandrel. Pre-formed bend 205 can correspond to the angle between the body lumen in which inner catheter 100 is inserted and a second body lumen that branches from the first body lumen. For example, pre-formed bend 205 can correspond to the angle between the trachea 302 and either the right or left main bronchus 304 or 306. The pre-formed bend (if provided) of outer catheter 100 can be formed using a similar method.

In some embodiments, in which two inner catheters 200 can be inserted through the lumen(s) 108 of outer catheter 100, the second inner catheter 200 can be advance independently of first inner catheter 200 or dependently with first inner catheter 200. For example, as shown in FIGS. 6A, 6B, and 7-10, a first inner catheter 200a can be simultaneously advanced into the left main bronchus 304 while a second inner catheter 200b is advanced into the right main bronchus 306 by virtue of pre-formed bend 205.

In addition to or in place of pre-formed bend 205, inner catheter 200 can be provided with an articulation mechanism, such as catheter pull wires as known in the art, for maneuvering distal end portion 206 to a target body lumen. Thus, in some embodiments, inner catheter 200 can be manually articulated. Where catheter system 10 includes more than one inner catheter (e.g., inner catheters 200a and 200b), catheter 200a and catheter 200b can be articulated independently of each other, which can allow distal end portion 206 to be articulated to enter a lobar bronchus 308 from a main bronchus 304 or 306 (see illustration of lung passageways in FIG. 9, for example). In some embodiments, distal end portion 206 can include location indicator(s), such as marker bands 215 that extend around the outer contour of elongated body 202 at distal end portion 206 of inner catheter 200 as shown in FIGS. 1 and 5. Marker bands 215 can be detected using imaging technology, for example, fluoroscopy or ultrasound, thereby allowing the medical practitioner to visualize the location of distal end portion 206 of inner catheter 200. The medical practitioner can articulate distal end portion 206 using pull wire(s) to enter one of the lobar bronchi 308, or deeper into a bodily passageway (e.g., segmental bronchi 310 and subsegmental bronchi).

In some embodiments, inner catheters 200a and 200b can have distinguishing location markers, thereby allowing the medical practitioner to differentiate between the two catheters 200a and 200b. For example, inner catheter 200a can have two marker bands 215, and inner catheter 200b can have three marker bands 215. Marker bands 215 can be used by the medical practitioner to verify that the inner catheters 200a and 200b are properly positioned in their respective target body lumen (e.g., left and right main bronchi 306 and 304), and that inner catheters 200a and 200b have not become twisted so as to accidentally be positioned in the respective body lumen intended for the other inner catheter. In some embodiments, distinguishing location makers can be different shapes, symbols (e.g., chevrons, which can also indicate twisting of the catheter by movement of the chevron's apex), and letters. For example, inner catheter 200a can have a marker 215 that is shaped as an "R," and inner catheter 200b can have a marker 215 that is shaped as an "L." In this example, a medical practitioner can easily recognize that the inner catheter with an "R" marker is the right inner catheter 200a and the inner catheter with an "L" is the left inner catheter 200b. For example, inner catheter 200a can have a marker 215 that is a chevron whose apex points left when inner catheter 200 is at one rotational orientation and whose apex then points right when inner catheter 200 is twisted 180 degrees to another rotational orientation.

Distal end portion 106 of outer catheter 100 and distal end portion 206 of inner catheter 200 (e.g., catheters 200a and 200b) can be shaped to be atraumatic to mitigate or prevent damage to the body lumen wall in which the distal end portions are inserted. For example, the outer edges of distal tip 118 can be rounded or have a large radius curve as shown in FIGS. 4A and 4B. The distal tip 211 of distal end portion 206 of inner catheter 200 can be rounded and have a large radius as shown in FIGS. 1, 2 and 7-11. FIG. 5 illustrates an inner catheter 200' which is a variation of earlier described inner catheter 200. As shown, inner catheter 200' includes an atraumatic distal tip 211' of distal end portion 206 that is bullet shaped, or conical shaped. A bullet shaped distal end portion 206 helps mitigate damage to the body lumen wall and helps guide inner catheter 200 from one body lumen into a branching body lumen. The conical shaped tip 211' can have one or more openings 207a and 207b for allowing a substance to pass through. Openings 207a and 207b can be in communication with one or more lumens in the catheter 200'. For example, in some embodiments in which inner catheter 200' has two lumens (e.g., lumens 208 and 210 in FIG. 3A), opening 207a can be in communication with one lumen (e.g., lumen 208), and opening 207b can be in communication with the other lumen (e.g., lumen 210). In such embodiments, catheter 200' can be used to deliver substances (e.g., saline or medicinal fluids) via hole 207b and lumen 210, and catheter 200' can be used to remove substances (e.g., aspirating mucus or other bodily fluids) via hole 207a and lumen 208.

Catheter 200' can include one or more flexibility mechanisms to enhance the flexibility at bend 205 or other points on elongated body 202 where flexibility is required. Such flexibility mechanisms can include, for example, coiled wire 207 or living hinge 209, or a combination thereof. In the embodiment of FIG. 5, both coiled wire 207 and living hinge 209 are provided at bend 205. Catheter 200' is also provided with a directional indicator marker 217 at proximal end portion 204, which provides the medical practitioner with a visual reference proximal end portion 204 as to what radial direction angled distal end portion 206 is pointing. When catheter 200' is configured to extend to the bronchi for aspiration, drug delivery, or other procedure (e.g., catheter 200' has a lumen for aspiration and/or a lumen for drug delivery as described above for catheter 200), indicator 217 clearly indicates to the medical practitioner which of the two main bronchi the distal end portion 206 resides, thereby ensuring that the procedure is conducted on the targeted lung.

In some embodiments, inner catheter 200 can also include a key joint component that corresponds to a key joint component on outer catheter 100. The corresponding key joint components can fix the rotational orientation of elongated body 202 of inner catheter 200 relative to that of elongated body 102 of outer catheter 100, and can also serve as a positional indicator as to what radial direction angled distal end portion 206 is pointing. When catheter system 10 is inserted in a body lumen (e.g., trachea), coupling the corresponding key joint components of inner and outer catheters 200 and 100 can ensure that inner catheter 200 is rotationally oriented about longitudinal axis 20 so that angled distal end portion 206 is directed toward the target branching lumen (e.g., a main bronchus). In some embodiments, the key joint components of inner catheter 200 and outer catheter 100 can be a corresponding key and keyway, respectively, or in some embodiments, a corresponding keyway and key, respectively. In some embodiments, the key joint components of inner catheter 200 and outer catheter 100 can be corresponding non-circle shapes of the contours of inner catheter 200 and outer catheter 100, for example, polygons such as squares, ovals, and any other suitable shape.

In some embodiments, the key joint components can allow limited number of different rotational orientations of elongated body 202 of inner catheter 200 relative to that of elongated body 102 of outer catheter 100. For example, outer catheter 100 can define an oval contoured lumen. An inner catheter 200 that has a corresponding contoured oval shape can be inserted in the oval contoured lumen of outer catheter 100 at a first orientation and at a second orientation that is 180 degrees from the first orientation. As another example, outer catheter 100 can define a square contoured lumen. An inner catheter 200 that has a corresponding contoured square shape can be inserted in the square contoured lumen of outer catheter 100 at a first orientation, at a second orientation that is 90 degrees from the first orientation, at a third orientation that is 180 degrees from the first orientation, and at a fourth orientation that is 270 degrees from the first orientation. It should be understood that these configurations of key joint components that allow a limited number of different rotational orientations of elongated body 202 of inner catheter 200 relative to that of elongated body 102 of outer catheter 100 are described as non-limiting examples only.

FIGS. 3A and 3B illustrate catheters 200 (specifically, catheters 200a and 200b) each having elongated body 202 with a key joint component. FIGS. 3A and 3B is schematic illustration that does not show angling of distal end portion 206 at bend 205 described above. In some embodiments, the outer contour can include a first hollow cylindrical portion 212 that defines first lumen 208, and second hollow cylindrical portion 214 that defines second lumen 210. First cylindrical portion 210 connects to second cylindrical portion 214 along the length of elongated body 202 at intermediate portion 216. Second cylindrical portion 214 can have a smaller outer diameter than first cylindrical portion 212. The outer surface of second cylindrical portion 214 is raised from the outer surface of first cylindrical portion 212. Accordingly, second cylindrical portion 214 functions as a key joint component, and, in the particular embodiment shown, as a key. The key joint component of elongated body 202 corresponds to a key joint component on outer catheter 100 to which catheter 200 can be coupled. For example, when the key joint component on elongated body 202 is a key (as shown), the key joint component on outer catheter 100 is a keyway (as shown) that corresponds to the key on elongated body 202. Alternatively, when the key joint component on elongated body 202 is a keyway, the key joint component on outer catheter 100 is a key that corresponds to the keyway on elongated body 202.

Elongated body 102 can define a lumen 108 having an inner surface that is contoured to correspond to the contour of the outer surface of elongated body 202 of inner catheter 200. In some embodiments, as shown in FIGS. 3A and 3B, lumen 108 includes a first circular channel portion 110 and a second semicircular channel portion 112 extending outward from the periphery of first circular channel portion 110. A surface of lumen 108 forming semicircular channel portion 112 is recessed from the surface of lumen 108 forming circular channel portion 110 The radius of second semicircular portion 112 can be smaller than the radius of first circular channel portion 110. Semicircular portion 112 can function as the key joint component of catheter 100, and, in the particular embodiment shown, as the keyway that corresponds to the key on elongated body 202 of inner catheter 200. In some embodiments, first and second channel portions 110 and 112 can be semicircular shapes that together form a contour that is a circle. In some embodiments, first and second channel portions 110 and 112 can be other shapes that together form a contour that is not a circle. For example, first channel portion 110 can be circular, and second channel portion 112 can be square. In some embodiments, first and second channel portions 110 and 112 can together form other shapes such as ovals, stars, and polygons. The contour of the outer surface of elongated body 202 of inner catheter 200 corresponds with the shape of the inner surface of first and second channel portions 110 and 112.

Key joint component 214 on inner catheter 200 can be coupled with a key joint component 112 of lumen 108 in outer catheter 100, fixing the rotational orientation of inner catheter 200 relative to that of outer catheter 100 about longitudinal axis 20 of the body lumen. In some embodiments, key joint component 214 on inner catheter 200 is coupled to key joint component 112 of outer catheter 100 prior to inserting distal end portion 106 into the body lumen. In some embodiments, key joint component 214 on inner catheter 200 is coupled to key joint component 112 of outer catheter 100 after distal end portion 106 is advanced into trachea 302 by subsequently advancing catheter 200 through lumen 108.

The direction at which angled distal end portion 206 extends from the longitudinal axis 20 of the body lumen can be aligned with another body lumen that branches from the body lumen in which the outer catheter 100 is inserted, for example, the left or right main bronchus 304 or 306, by rotating outer catheter 100. As noted, key components 214 and 112 can be used as a visual indicator of the rotational orientation of angled distal end portion 206.

In some embodiments, the key joint component of inner catheter 100 and outer catheter 200 can extend entirely from respective proximal end portions 104 and 204 to respective distal end portions 106 and 206. In some embodiments, the key joint components of inner catheter 100 and outer catheter 200 can only extend along a partial length between respective proximal end portions 104 and 204 and distal end portions 106 and 206.

In some embodiments having two inner catheters 200a and 200b with pre-formed bends 205, the corresponding key components of inner catheters 200a and 200b with outer catheter 100 can be configured to fix the rotational orientation of inner catheters 200a and 200b relative to each other, and align the direction of each angled distal end portions 206 to be toward the target branching lumen. For example, the key components can be configured to orient the angled distal end portions 206 of catheters 200a and 200b so as to bend away from each other, as illustrated in FIG. 2. In this manner, when catheter system 10 is inserted into a body lumen such as the trachea, the rotational orientation of inner catheters 200a and 200b can be fixed relative to longitudinal axis 20 of the trachea. The angled distal end portions 206 of catheters 200a and 200b can be then be extended to easily access a respective main bronchus by virtue of the pre-formed bend 205 and fixed rotational orientation. As illustrated in the embodiments of FIGS. 7-11, for example, when outer catheter 100 is inserted in a trachea 302, the key components of outer catheter 100 and inner catheters 200a and 200b can align distal end portion 206 of catheter 200b towards left main bronchus 304 and distal end portion 206 of catheter 200a towards right main bronchus 306. In some embodiments, inner catheters 200a and 200b are rotationally oriented so that its distal end portion 206 extends from longitudinal axis 20 of the body lumen about 180 degrees from the direction at which the distal end portion 206 of the inner catheter 200b extends from the longitudinal axis 20 of the body lumen.

FIGS. 4A-4D illustrates cross-sectional views showing exemplary catheter and lumen configurations for outer catheter 100 and inner catheter(s) 200. It should be understood that the configurations of catheter system 10 illustrated in the FIGS. 4A-4D are shown as non-limiting examples only. In FIG. 4A, the contour of the outer surface of outer catheter 100 can have an oval shape, for example. Elongated body 102 defines two circular lumens 108. Each lumen 108 receives a circular inner catheter 200a or 200b. Elongated bodies 202 of inner catheters 200a and 200b each define one lumen 208. In this configuration, in contrast with the configuration of inner and outer catheters 200a, 200b, and 100 of FIGS. 3A and 3B, inner catheters 200a and 200b of FIG. 4A are not keyed with outer catheter 100. Because inner catheters 200a and 200b are not keyed with outer catheter 100, accessories or parts at proximal ends 204 of inner catheters 200a and 200b, for example ports 218 and 220, can be used to align the direction of pre-formed bends 205. Thus, ports 218 and 220 can serve the same purpose as direction indicator 217 described above with respect to the embodiment of FIG. 5.

In FIG. 4B, the contour of the outer surface of outer catheter 100 can have an oval shape, for example. Elongated body 102 defines two lumens 108 having a non-circle shape, for example, an oval. Each lumen 108 receives an inner catheter 200a or 200b having a contoured outer surface with a corresponding non-circle shape, for example, a corresponding oval shape. Elongated bodies 202 of inner catheters 200a and 200b each define two lumens 208 and 210. In this configuration, inner catheters 200a and 200b are keyed with outer catheter 100. In some embodiments, lumens 108 can be circular as shown in FIG. 4A, and inner catheters 200a and 200b can have corresponding circular contours. In such circular embodiments, outer catheter 100 would not be keyed with catheters 200a and 200b.

Figure 4C:
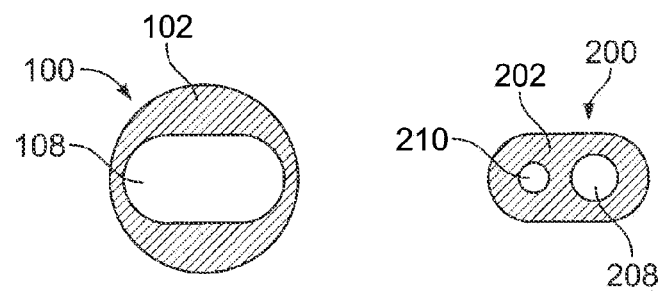

In FIG. 4C, the contour of the outer surface of outer catheter 100 can have a circular shape. Elongated body 102 defines one lumen 108 having a non-circle shape, for example, an oval. Lumen 108 receives an inner catheter 200 having a contoured outer surface with a corresponding non-circle shape, for example, a corresponding oval shape. Elongated body 202 of inner catheter 200 defines two lumens 208 and 210. In this configuration, single inner catheter 200 is keyed with outer catheter 100.

Figure 4D:
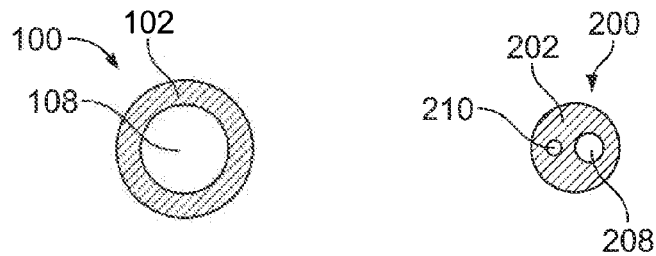

In FIG. 4D, the contour of the outer surface of outer catheter 100 can have a circular shape. Elongated body 102 defines one lumen 108 having a circular shape. Lumen 108 receives an inner catheter 200 having a contoured outer surface with a corresponding circular shape. Elongated body 202 of inner catheter 200 defines two lumens 208 and 210. In this configuration, single inner catheter 200 is not keyed with outer catheter 100. Accessories or parts at proximal end 204 of inner catheter 200, for example ports 218 and 220, can be used to align the direction of pre-formed bend 205.

A method of using catheter system 10 according to some embodiments will now be described with reference to FIGS. 6A, 6B, and 7-10. In the method illustrated in FIGS. 6A, 6B, and 7-10, outer catheter 100 is inserted into a trachea 302 through the mouth or nose or by an incision in the throat. The key joint component of each inner catheter 200 is coupled with the respective key joint components of outer catheter 100. For example, the key joint components can be coupled by aligning a key on elongated body 202 of inner catheter 200 with a keyway in a lumen of outer catheter 100, and then sliding inner catheter 200 within the lumen of outer catheter 100. As illustrated in FIG. 6A, inner catheters 200a and 200b are coupled to outer catheter 100, and catheter 100 is inserted in trachea 302 and advanced through trachea 302. (FIG. 6B is similar to FIG. 6A, but illustrates inner catheters 200a and 200b having conical distal end portions 206 as described above regarding FIG. 5.) Coupling the key joint components of inner catheters 200a and 200b with the key joint components of outer catheter 100 fixes the rotational orientation of inner catheters 200a and 200b about longitudinal axis 20. The orientation of inner catheter 200a is fixed so that the direction at which pre-formed bend 205 of its distal end portion 206 extends from longitudinal axis 20 is aligned with the right main bronchus 306. Similarly, the orientation of inner catheter 200b is fixed so that the direction at which the pre-formed bend of its distal end portion 206 extends from longitudinal axis 20 is aligned with the left main bronchus 304. In some embodiments, outer catheter 100 can be inserted in the trachea first, and inner catheters 200a and 200b can then be slid into the lumen(s) of inner catheter 100, coupling the respective key joint components.

Returning to FIGS. 6A and 6B, outer catheter 100 with inner catheters 200a and 200b disposed therein is advanced through trachea 302. As shown in FIG. 7, distal end portions 206 of inner catheters 200a and 200b are advanced downward and towards the left and right main bronchi 304 and 306. The position of outer catheter 100 is maintained in the trachea 302. Distal end portions 206 can be substantial straight (not angled relative to longitudinal axis 20 of the body lumen) while within outer catheter 100, but as distal end portions 206 extend from distal end portion 106, distal end portions 206 begin to angle away from longitudinal axis 20 as shown in FIGS. 8-10. In some embodiments, after distal end portions 206 have been advance a certain distance, pre-formed bend 205 cause distal end portions 206 to contact the side walls of trachea 302.

As shown in FIGS. 7 and 8, distal ends 206 of inner catheters 200a and 200b can be further advanced downward and towards the left and right main bronchi 304 and 306. Distal end portions 206 can slide down the side walls of trachea 302 (see FIG. 7) until the distal end portion 206 of inner catheter 200a is on the right of the carina 303 at the intersection of the trachea 302 and the right main bronchus 306 (see FIG. 8), and distal end portion 206 of inner catheter 200b is on the left of the carina 303 at the intersection of the trachea 302 and the left main bronchus 304 (see FIG. 8). A medical practitioner of catheter system 10 advances distal end portion 206 of inner catheter 200b towards left main bronchus 304 and distal end portion 206 of inner catheter 200a towards right main bronchus 306 by advancing the respective elongated bodies 202 within the lumen(s) of catheter 100.

As shown in FIG. 9, distal end portion 206 of inner catheter 200a can be advanced into the right main bronchus 306, and distal end portion 206 of inner catheter 200b can be advanced into left main bronchus 304 by further advancing the respective elongated bodies 202 within the lumen(s) of catheter 100. In the embodiment shown, no articulation using pull wires of elongated body 202 is needed to advance elongated body 202 into the left or right main bronchus 304 or 306. If the direction at which the pre-formed bend 205 extends away from longitudinal axis 20 of trachea 302 is aligned with the desired main bronchus, the pre-formed bend guides elongated body 202 into the desired bronchus as elongated body 202 is advanced within outer catheter 100. In some embodiments, distal end portion 206 can contact an inferior surface of the main bronchus 304 or 306 during advancement within main bronchus 304 or 306. In some embodiments, the pre-formed bend can be configured to cause distal end portion 206 to contact a superior surface of the main bronchus 304 or 306 during advancement within main bronchus 304 or 306. Distal end portions 206 of inner catheters 200a and 200b can be advanced within the main bronchi 304 and 306 until distal end portions 206 reach the intersection of the main bronchi 304 and 306 and the lobar bronchi 308.

In some embodiments, catheter system 10 can be inserted in a body lumen with one or more inner catheters 200 slightly extended from distal end portion 106 of outer catheter 100 (see, e.g., FIG. 8). Outer catheter 100 can be advanced into the body lumen until the medical practitioner feels distal end portion 206 of inner catheter(s) 200 contact a second body lumen that branches from the first body lumen, for example, the left or right main bronchus 304 or 306 near the carina 303. At this position, the medical practitioner can cease further advancement of outer catheter 100 and begin individual (or simultaneous, in some embodiments) advancement of each inner catheter 200. In this manner, outer catheter 100 is not advanced too far so as to mistakenly extend into one of the main bronchi, and consequently ensures that each inner catheter 200 will be advanced into the targeted main bronchus.

In some embodiments, catheter system 10 can include outer catheter 100 and a single inner catheter 200 disposed in lumen 108 defined by elongated body 102. Outer catheter 100 and inner catheter 200 are inserted into trachea 302 through the mouth or nose or by an incision in the throat. The direction at which pre-formed bend 205 extends from longitudinal axis 20 is aligned with the desired main bronchus 304 or 306. Single inner catheter 200 can be selectively deployed into either the desired main bronchus 304 and 306 by advancing elongated body 202 through elongated body 102 of outer catheter 100. As elongated body 202 of inner catheter 200 is advanced, distal end portion 206 extends away from distal end portion 106 of inner catheter 200 and begins extending away from longitudinal axis 20. During advancement of inner catheter 200, the position of outer catheter 100 can be maintained within trachea 302. Distal end portion 206 of inner catheter 200 can be advanced into the desired main bronchus 304 or 306 by further advancing elongated body 202 within lumen 108 of outer catheter 100. Pre-formed bend 205 guides elongated body 202 into the bronchus 304 or 306 aligned with the direction that pre-formed bend 205 extends from longitudinal axis 20.

In some embodiments having a single catheter 200, after distal end portion 206 has been deployed in a desired main bronchus, for example, right main bronchus 306, distal end portion 206 can be retracted from right main bronchus 306 by advancing elongated body 202 in an opposite direction. Once distal end portion 206 is out the right main bronchus 306 and in trachea 302, the direction at which pre-formed bend 205 extends from longitudinal axis 20 can be realigned with left main bronchus 304 by either rotating inner catheter 200 independent from outer catheter 100 or by rotating inner catheter 200 with outer catheter 100. In some embodiments, the medical practitioner can use directional indicator marker 217 and/or key joint component 214 (if provided) to help identify and fix the rotational orientation of inner catheter 200 in trachea 302 and realign pre-formed bend 205 with left main bronchus 304. Inner catheter 200 can then be selectively deployed into left main bronchus 306 by advancing elongated body 202 through elongated body 102 of outer catheter 100 as described above. Pre-formed bend 205 guides elongated body 202 into left main bronchus 304. Afterwards, inner catheter 200 and outer catheter 100 can be removed from the body.

Catheter system 10 having only one inner catheter 200 can be useful for performing procedures in body lumens having a small diameter. For example, in pediatrics, the diameter of an infant's trachea is small and can only receive a single inner catheter 200 and endotracheal tube. In some embodiments, the endotracheal tube can serve as outer catheter 100.

In some embodiments, distal end portion 206 of inner catheter 200 can be further inserted into the lobar bronchi 308, segmental bronchi 310, and subsegmental bronchi by articulating distal end portion 206 with pull wire. In some embodiments, distal end portion 206 can include location indicator(s), such as marker bands 215, to detect the location of distal end portion 206. With location provided by the marker bands 215, a medical practitioner can articulate distal end portion 206 using pull wire(s) to angle and maneuver distal end portion 206 (in addition to the angle created by pre-formed bend 205) to enter one of the lobar bronchi 308, or deeper into a bodily passageway (e.g., segmental bronchi 310 and subsegmental bronchi).

The location of inner catheters 200a and 200b within the left and right main bronchi 304 and 306, or elsewhere within the body, can be verified using acoustic devices or a light source as described above. At this point, inner catheters 200a and 200b can be used to perform various diagnostic and therapeutic procedures within the main bronchi 304 and 306, for example, deliver medicinal fluids (including, for example, aerosolized liquid or powder medicinal drugs) and/or aspirate mucus.

In some embodiments, catheter system 10 can include a catheter 400, for example, an endotracheal tube. In such embodiments, outer catheter 100 can serve as a deliver catheter for inner catheter(s) 200 while catheter 400 serves as an endotracheal tube. FIG. 10 illustrates a catheter system 10, which includes catheter 400, that is inserted in trachea 302. Catheter 400 allows outer catheter 100 and inner catheter(s) 200 to be easily inserted into and removed from the trachea 302. In particular, FIG. 10 illustrates catheter 400 having an elongated body 402 and an expandable support member 420 (shown in its inflated state) according to an embodiment. The expandable support member 420 shown in FIG. 10 is an inflatable balloon mounted on an outer surface of elongated body 402. Elongated body 402 can define one or more lumens. Outer catheter 100 and inner catheter(s) 200 can pass through a lumen defined by elongated body 402. While one balloon 420 is illustrated, it should be understood that more than one balloon 420 can be provided along the length of body 402 of catheter 400. Such balloon (s) 420 can serve to selectively engage the body lumen and further secure catheter 400 in position in trachea 302, for example, at the center of trachea 302. Because catheter 400 is secured in position in trachea 302, catheter 400 can also help position outer catheter 100 and inner catheter(s) 200 at a desired location within the body lumen by passing outer catheter 100 and inner catheter(s) through a lumen in elongated body 402 of catheter 400.

Balloon 420 can be donut-shaped so as to have a circular body 421 with a central axial opening. Elongated body 402 extends through the axial opening of the balloon 420. The inflatable balloon can be filled by any suitable gas or liquid, for example, air. When the balloon 420 is inflated to contact the wall of a body lumen and stabilize elongated body 402, balloon 420 and elongated body 402 can occlude the body lumen, but a lumen defined by elongated body 402 permits the continued passage of bodily fluid or gas through the body lumen via the lumen of elongated body 402. For example, inhaled or exhaled air through the trachea 302 or main bronchi 304 and 306 is permitted with minimal obstruction by the presence of catheter 400 having a catheter system 10 coupled thereto, thereby reducing or eliminating the likelihood that the catheterization will detrimentally affect the patient's natural bodily functions. In some embodiments, expandable support member 420 can be a non-inflatable, mechanical expandable support member (e.g., formed of a shape-memory material) such as described in U.S. patent application Ser. No. 12/873,977. Exemplary expandable support members that can be employed as expandable support member(s) 420 are described in U.S. patent application Ser. No. 12/873,977, filed Sep. 1, 2010, which is incorporated by reference in its entirety herein.

In some embodiments, catheter 400 can have one balloon 420 that is an inflatable bubble on one side of elongated body 402. In some embodiments, catheter 400 can have two balloons 420 that are inflatable bubbles on opposite sides of elongated body 402.

In embodiments using catheter 400 as shown in FIG. 10, catheter 400 can be inserted in trachea 302 inserted into a trachea 302 through the mouth or nose or by an incision in the throat. Outer catheter 100 and inner catheter(s) 200 can pass through a lumen defined by elongated body 402 of catheter 400 and advanced in a trachea 302 as described above regarding FIGS. 6A, 6B, and 7. Inner catheter(s) 200 can then be deployed as described above regarding FIGS. 7-10. After performing a desired procedure (e.g., aspiration of the lungs), outer catheter 100 and inner catheter(s) 200 can be withdrawn from the body while catheter 400 remains in place within the trachea 302.

In some embodiments, catheter 400, outer catheter 100, and inner catheter(s) 200 can be inserted a body lumen with one or more inner catheters 200 slightly extended from the distal end portion 106 of outer catheter 100 (see, e.g., FIG. 8) and from the distal end of elongated body 402. Catheter 400, outer catheter 100, and inner catheter(s) 200 can then be simultaneously advanced into the body lumen until the medical practitioner feels distal end portion 206 of inner catheter(s) 200 contact a second body lumen that branches from the first body lumen, for example, the right or left main bronchus 304 or 306 near the carina 303. At this position, the medical practitioner can cease further advancement of catheter 400 and outer catheter 100 and begin individual (or simultaneous, in some embodiments) advancement of each inner catheter(s) 200. In this manner, catheter 400, as well as outer catheter 100, is not advanced too far so as to mistakenly extend into the second body lumen, for example, one of the main bronchi, and consequently ensures that each inner catheter(s) 200 will be advanced into the targeted bronchus. In some embodiments, when advancement of catheter 400 is stopped, expandable support member 420 is engaged with the side wall of the body lumen to secure catheter 400 in place within the body lumen, as shown in FIG. 10.

For example, catheter system 10 can include outer catheter 100 and two inner catheters 200a and 200b slidably disposed therein in one or more lumen(s) 108. Outer catheter 100 and two inner catheters 200a and 200b can pass through catheter 400 (if provided) which is inserted in a patient's mouth or an incision in the throat. The direction at which pre-formed bend 205 of inner catheter 200a extends from longitudinal axis 20 is aligned with right main bronchus 306, and the direction at which pre-formed bend 205 of inner catheter 200b is aligned with left main bronchus 306. Catheter 400, outer catheter 100, and inner catheters 200a and 200b, each having a distal end portion 206 slightly extended from distal end portion 106 of outer catheter 100, can then be simultaneously advanced into trachea 302 until the medical practitioner feels distal end portions 206 of inner catheters 200a and 200b contact the right and left main bronchi 306 and 304. At this position, the medical practitioner can cease further advancement of catheter 400 and outer catheter 100. In this manner, catheter 400, as well as outer catheter 100, is not advanced too far so as to mistakenly extend into one of the main bronchi 306 or 304, and consequently ensures that each inner catheter 200a and 200b will be advanced into the targeted bronchus 306 and 304, respectively. In addition, by virtue of inner catheters 200a and 200b each being advanced in a different main bronchus, the medical practitioner can be prevented from advancing catheters 400 and 100 past carina 303 into one of the main bronchi. Moreover, the inner catheter 200a and 200b being in a different main bronchus helps properly position outer catheter 100 and catheter 400 in trachea 302, whereafter the expandable member can be inflated (e.g., expandable member 420 for the embodiment of FIG. 10 having catheter 400, or expandable member 120 for the later-described embodiment of FIG. 11).

Inner catheters 200a and 200b can be advanced into the main bronchi 306 and 304 respectively, by simultaneously advancing elongated body 202 of inner catheter 200a and elongated body 202 of inner catheter 200b within elongated body 102 of outer catheter 100. As elongated bodies 202 of inner catheters 200a and 200b are advanced, distal end portions 206 of inner catheters 200a and 200b extend away from distal end portion 106 of inner catheter 200 and begin extending away from longitudinal axis 20. During advancement of inner catheters 200a and 200b, the position of outer catheter 100 can be maintained within trachea 302. Distal end portions 206 of inner catheters 200a and 200b can be advanced into main bronchus 306 and 304, respectively, by further advancing elongated bodies 202 of inner catheters 200a and 200b within lumen(s) 108 of outer catheter 100. Pre-formed bend 205 of inner catheter 200a guides elongated body 202 of inner catheter 200a into right main bronchus 306, and pre-formed bend 205 of inner catheter 200b guides elongated body 202 of inner catheter 200b into the left main bronchus 304.

After performing the desired procedures in left and right main bronchus 304 and 306 (or in further branching bronchi, if distal end portions 206 are articulated deeper), inner catheters 200a and 200b, along with outer catheter 100, can be withdrawn from the body while catheter 400 remains in place within trachea 302 (and secured in position via expandable member 420). Outer catheter 100 and inner catheters 200a and 200b can be reinserted into the body through catheter 400 to perform another procedure, for example, aspiration of target bronchi, when needed.

In some embodiments, catheter system 10 can include outer catheter 100 and one or more inner catheters, and outer catheter 100 can be provided with one or more expandable support member(s) 120 (similar to balloon 420 provided with catheter 400), which secure outer catheter 100 in place in a body lumen, for example, a trachea or a main bronchus. In such embodiments, outer catheter 100 can serve as an endotracheal tube, for example (in lieu of a separate catheter 400 serving as an endotracheal tube as described above with reference to FIG. 10). Support member(s) 120 can be expanded once distal end portion 106 has been advance through trachea 302 to the desired position within as illustrated in FIG. 11. In particular, FIG. 11 illustrates catheter system 10 having outer catheter 100 with expandable support member 120 according to an embodiment. The expandable support member 120 shown in FIG. 11 is an inflatable balloon (shown in its inflated state) mounted on an outer surface of elongated body 102. While one balloon 120 is illustrated, it should be understood that more than one balloon 120 can be provided along the length of body 102 of catheter 100, which can serve to engage the body lumen and further secure catheter 100 in position. The inflatable balloon can be filled by any suitable gas or liquid, for example, air.

In some embodiments, balloon 120 can completely occlude the gap between elongated body 102 and the side wall of trachea 302. In such embodiments, ventilation can occur through one or more lumens defined by elongated body 102. For example, inhaled or exhaled air through the trachea 302 or primary bronchi 304 and 306 is permitted with minimal obstruction by the presence of the lumen(s) in outer catheter 100 secured in place with inflated balloon 120, thereby reducing or eliminating the likelihood that the catheterization will detrimentally affect the patient's natural bodily functions. In other words, outer catheter 100 can also function as an endotracheal tube that establishes and maintains an airway that allows the passage of oxygen and carbon dioxide through trachea 302. In some embodiments, expandable support member 120 can be a non-inflatable, mechanical expandable support member (e.g., formed of a shape-memory material) such as described in U.S. patent application Ser. No. 12/873,977. Exemplary expandable support members that can be employed as expandable support member(s) 120 are described in U.S. patent application Ser. No. 12/873,977, filed Sep. 1, 2010.

Accordingly, a medical practitioner using a catheter system 10 and method as described above can easily intubate the left and right main bronchi 306 and 304 with inner catheters 200b and 200a without using an endoscopic procedure to ensure that the working catheter has actually entered left and right main bronchi 306 and 304.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. For example, although the figures illustrate the catheter system in the respiratory tract, the catheter system can be adapted for other body lumens such as the vascular system. Also, for example, FIG. 12 illustrates an outer catheter 100' which is a variation of earlier described outer catheter 100. As shown, outer catheter 100' includes an elongated body 102' that defines two channels 108'. Channels 108' can be separated by divider 109' formed in elongated body 102'. Distal end portion 106 can comprise a closed cap 120. Cap 120 can form an atraumatic tip, for example, a conical shape or rounded edge. Cap 120 can have openings 122a and 122b on the side walls of cap 120. Channels 108' can terminate proximal to openings 122a and 122b on the side walls of cap 120. Distal end portions 206 of inner catheters 200a and 200b will pass through openings 122a and 122b in cap 120 as catheters 200a and 200b are advanced because pre-formed bends 205 in distal end portions 206 (see, e.g., FIG. 2) biases distal end portions 206 towards the side wall. Once distal end portions 206 reach respective openings 122a and 122b, distal end portions 206 extend through openings 122a and 122b. Inner catheters 200a and 200b can then be deployed in a body lumen as described above regarding FIGS. 6A, 6B, and 7-10. Further, for example, FIG. 13 illustrates an outer catheter 100" which is a variation of earlier described outer catheter 100. As shown, outer catheter 100" includes an elongated body defines a first lumen 108a and a second lumen 108b through which inner catheters 200a and 200b, respectively pass. First lumen 108 has an opening 120a' on the side wall of elongated body 102. Second lumen 108 has an opening 120b' at the distal tip of distal end portion 106. Distal end portion 206 of inner catheter 200a will pass through opening 122a on the side wall of elongated body 102 as catheter 200a is advanced because pre-formed bend 205 in distal end portion 206 (see, e.g., FIG. 2) of catheter 200a biases distal end portion 206 towards the side wall of lumen 108 having opening 120b'. Once distal end portion 206 of inner catheter 200a reaches opening 122b', distal end portion 206 of catheter 200a extends through opening 122b'. Inner catheter 200a can then be deployed in a body lumen as described above regarding FIGS. 6A, 6B, and 7-10. Similarly, distal end portion 206 of inner catheter 200b will pass through opening 122b at the distal tip of distal end portion 106 as catheter 200b is advanced as described above in FIGS. 6A, 6B, and 7-10. In some embodiments, outer catheters 100' and 100", as shown in FIGS. 12 and 13, can be used with catheter 400. Therefore, such adaptations and modifications are intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance. The breadth and scope of the present invention should not be limited by any of the above-described exemplary embodiments, but should be defined only in accordance with the following claims and their equivalents.

What is claimed is:

1. A method of using a catheter in a pulmonary procedure, the method comprising:
   inserting a distal end of a catheter into a trachea of a patient such that the distal end of the catheter resides within the trachea or extends beyond the trachea into a body lumen of the patient;
   coupling a pump to a proximal end of the catheter, the pump being configured to create a suction at the distal end of the catheter;
   applying the suction at the proximal end of the catheter to remove a fluid from the body lumen through a lumen of the catheter;
   creating a sound at the distal end of the catheter with the applied suction, the sound being a vibration of the fluid as the fluid is removed by the lumen of the catheter by the applied suction;
   detecting a location of the sound by using a stethoscope on an outside body surface of the patient; and
   verifying a position of the distal end of the catheter within the body lumen based on the detected location of the sound.

2. The method of claim 1, wherein generating the sound at the distal end of the catheter comprises delivering fluid through a first lumen in the catheter to the distal end of the catheter; and removing the fluid delivered at the distal end of the catheter through a second lumen in the catheter.

3. The method of claim 2, wherein the fluid is a saline solution.

4. The method of claim 1, wherein during the removing of the fluid from the body lumen, the fluid passes an aerophone device at the distal end of the catheter to generate the sound.

5. The method of claim 4, wherein the aerophone device is a whistle.

6. The method of claim 1, wherein identifying the location of the sound comprises using the stethoscope on an outside surface of the patient's body to locate the sound.

7. The method of claim 1, wherein the sound is generated simultaneously with the applying of the suction.

* * * * *